(12) United States Patent
Kurishita et al.

(10) Patent No.: US 11,628,394 B2
(45) Date of Patent: Apr. 18, 2023

(54) GAS SEPARATION MEMBRANE MODULE

(71) Applicant: Asahi Kasei Kabushiki Kaisha, Tokyo (JP)

(72) Inventors: Yasutaka Kurishita, Tokyo (JP); Masato Mikawa, Tokyo (JP); Kimiya Murakami, Tokyo (JP); Azusa Yamanaka, Tokyo (JP); Masahiko Kawashima, Tokyo (JP)

(73) Assignee: Asahi Kasei Kabushiki Kaisha, Tokyo (JP)

( * ) Notice: Subject to any disclaimer, the term of this patent is extended or adjusted under 35 U.S.C. 154(b) by 910 days.

(21) Appl. No.: 16/323,666

(22) PCT Filed: Aug. 7, 2017

(86) PCT No.: PCT/JP2017/028630
§ 371 (c)(1),
(2) Date: Feb. 6, 2019

(87) PCT Pub. No.: WO2018/030356
PCT Pub. Date: Feb. 15, 2018

(65) Prior Publication Data
US 2021/0283550 A1 Sep. 16, 2021

(30) Foreign Application Priority Data

Aug. 8, 2016 (JP) .............................. JP2016-155856
Aug. 31, 2016 (JP) .............................. JP2016-169557
(Continued)

(51) Int. Cl.
*B01D 53/22* (2006.01)
*B01D 53/26* (2006.01)
(Continued)

(52) U.S. Cl.
CPC ......... *B01D 53/228* (2013.01); *B01D 53/229* (2013.01); *B01D 53/261* (2013.01);
(Continued)

(58) Field of Classification Search
None
See application file for complete search history.

(56) References Cited

U.S. PATENT DOCUMENTS 3,844,735 A    10/1974  Steigelmann et al.
5,057,641 A *  10/1991  Valus ..................... B01D 53/22
                                                        585/818
(Continued)

FOREIGN PATENT DOCUMENTS

EP    1803756 A1    7/2007
JP    H06-091130 A  4/1994
(Continued)

OTHER PUBLICATIONS

Rege et al., "Propane/propylene separation by pressure swing adsorption: sorbent comparison and multiplicity of cyclic steady states," Chemical Engineering Science, 57: 1139-1149 (2002).
(Continued)

*Primary Examiner* — Jason M Greene
(74) *Attorney, Agent, or Firm* — Morgan, Lewis & Bockius LLP

(57) ABSTRACT

The present disclosure provides a gas separation membrane module that has high, long-term utility. The present disclosure provides a gas separation membrane module that has: a housing; a gas separation membrane that is arranged inside the housing; and an adhesive part that fixes the gas separation membrane to the housing.

21 Claims, 8 Drawing Sheets

(30) Foreign Application Priority Data

| Feb. 15, 2017 | (JP) | JP2017-026214 |
|---|---|---|
| Mar. 3, 2017 | (JP) | JP2017-040880 |
| Mar. 3, 2017 | (JP) | JP2017-040889 |

(51) Int. Cl.

| B01D 69/02 | (2006.01) |
|---|---|
| B01D 69/08 | (2006.01) |
| B01D 69/12 | (2006.01) |
| B01D 71/02 | (2006.01) |
| B01D 71/08 | (2006.01) |
| B01D 71/34 | (2006.01) |
| B01D 71/60 | (2006.01) |
| C07C 7/144 | (2006.01) |
| C09J 163/00 | (2006.01) |
| C09J 175/04 | (2006.01) |

(52) U.S. Cl.

CPC ............ *B01D 69/02* (2013.01); *B01D 69/08* (2013.01); *B01D 69/12* (2013.01); *B01D 71/022* (2013.01); *B01D 71/08* (2013.01); *B01D 71/34* (2013.01); *B01D 71/60* (2013.01); *C07C 7/144* (2013.01); *C09J 163/00* (2013.01); *C09J 175/04* (2013.01); *B01D 2325/023* (2013.01); *B01D 2325/20* (2013.01)

(56) References Cited

U.S. PATENT DOCUMENTS

| 5,818,228 | A | * | 10/1998 | Menon | G01R 33/44 |
| | | | | | 324/300 |
| 6,290,756 | B1 | * | 9/2001 | Macheras | B01D 53/22 |
| | | | | | 156/294 |
| 6,648,945 | B1 | * | 11/2003 | Takeda | B01D 69/12 |
| | | | | | 95/46 |
| 2004/0000231 | A1 | | 1/2004 | Bikson et al. | |
| 2004/0045893 | A1 | * | 3/2004 | Watanabe | B01D 67/0083 |
| | | | | | 210/321.79 |
| 2011/0036237 | A1 | | 2/2011 | Okada et al. | |
| 2011/0198558 | A1 | | 8/2011 | Okai et al. | |
| 2014/0245884 | A1 | | 9/2014 | Feng et al. | |
| 2015/0025293 | A1 | | 1/2015 | Feiring et al. | |
| 2016/0008766 | A1 | | 1/2016 | Aburaya et al. | |
| 2016/0236151 | A1 | * | 8/2016 | Liu | B01D 53/228 |
| 2017/0275233 | A1 | * | 9/2017 | Boone | C08K 5/18 |

FOREIGN PATENT DOCUMENTS

| JP | 2007-203298 | A | 8/2007 |
|---|---|---|---|
| JP | 4469635 | B2 | 5/2010 |
| JP | 2010-162447 | A | 7/2010 |
| JP | 2014-208325 | A | 11/2014 |
| JP | 2014-533193 | A | 12/2014 |
| JP | 2015-508710 | A | 3/2015 |
| WO | 2006/043386 | A1 | 4/2006 |
| WO | 2009/093666 | A1 | 7/2009 |
| WO | 2012/167362 | A1 | 12/2012 |
| WO | 2013/130923 | A1 | 9/2013 |
| WO | 2015/141686 | A1 | 9/2015 |

OTHER PUBLICATIONS

Kumai, "Material Evaluation Technology with Pulse NMR," Ricoh Technical Repod No. 40, 136-143 (2015) (see English abstract).

Lee et al., "Antiplasticization and plasticization of Matrimid asymmetric hollow fiber membranes—Part A. Experimental," Journal of Membrane Science, 350: 232-241 (2010).

Al-Juaied et al., "Performance of natural gas membranes in the presence of heavy hydrocarbons," Journal of Membrane Science, 274: 227-243 (2006).

Surveying Project Results Presentation Conference of the Japan Petroleum Energy Center, vol. 2012, pp. 322-332 (Jun. 1, 2012) (see partial English translation).

International Search Report issued in corresponding International Patent Application No. PCT/JP2017/028630 dated Nov. 7, 2017.

International Preliminary Report on Patentability and Written Opinion issued in corresponding International Patent Application No. PCT/JP2017/028630 dated Feb. 12, 2019.

* cited by examiner

FIG. 2
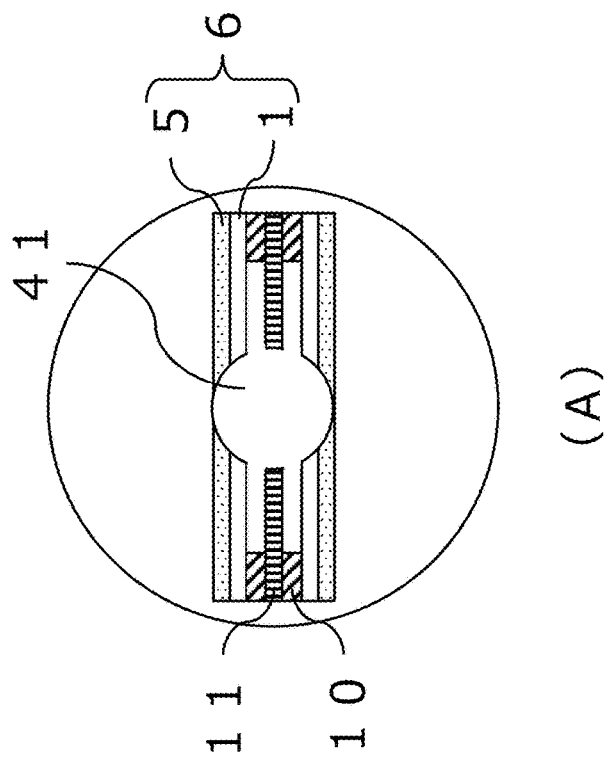
(A)
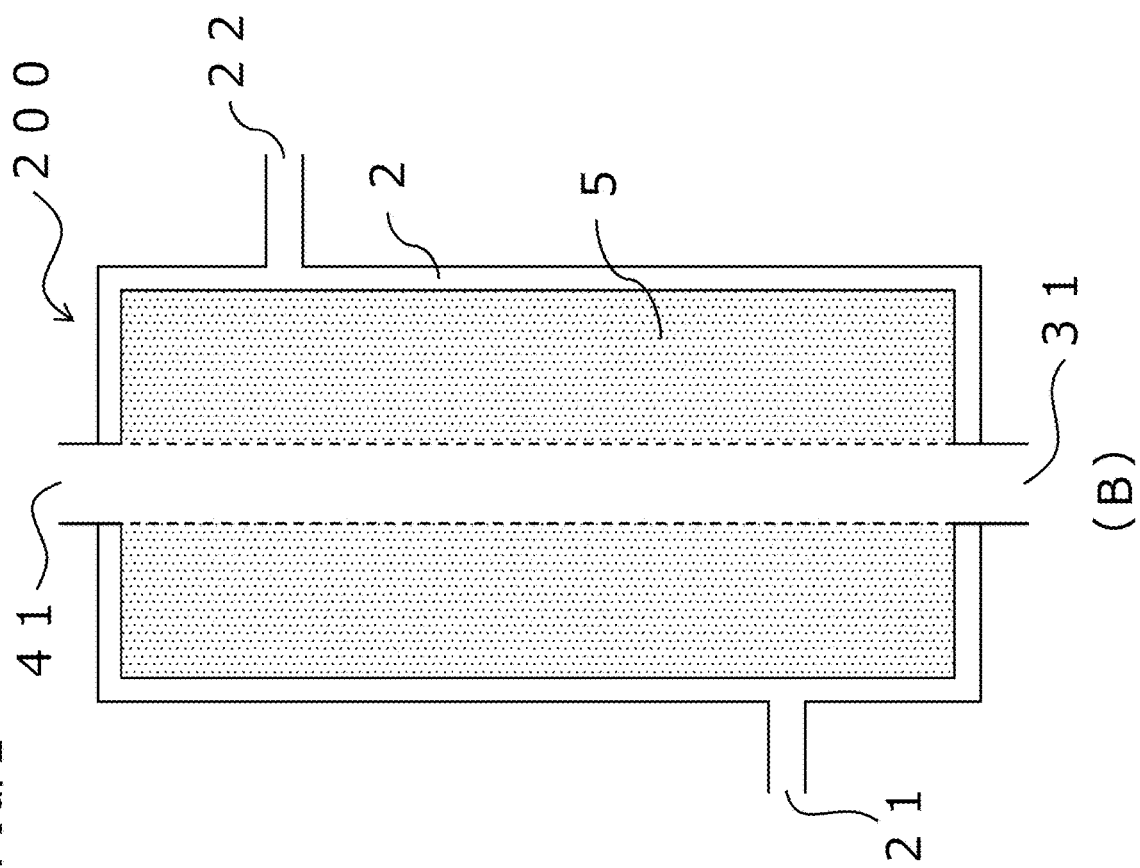
(B)

GAS SEPARATION MEMBRANE MODULE

FIELD

The present invention relates to membrane modules for gas separation, which are significantly practical for a long period of time. The membrane modules for gas separation of the present invention exhibit an excellent function of the separation of, in particular, olefins.

BACKGROUND

Gas separation/condensation with a gas separation membrane is a highly energy efficient, energy-saving, and highly safe method as compared to a distillation method, a high-pressure adsorption method, etc. Pioneering practical examples in the pertinent field include gas separation and condensation, hydrogen separation in the production of ammonia, etc., using gas separation membranes. Recently, gas separation membranes for the separation of hydrocarbon gases, such as the separation of an olefin gas and a paraffin gas, have been intensively studied.

Membrane modules for the separation of a hydrocarbon gas are composed of a porous membrane, a housing, and an adhesive. A gas separation active layer may be disposed on the surface of the above porous membrane to enhance the gas separation performance of the membrane module (PTLs 1 and 2). Such a gas separation active layer may optionally contain a metal (e.g., a metal salt) (PTLs 3 and 4).

In order to improve the practicality of the membrane module for gas separation, it is desirable that each of the constituent members of the module be chemically resistant.

High purity gases obtained by purification with gas separation membranes are sometimes used in the field of semiconductors. In this application, it is necessary that the gases be highly pure. In order to satisfy this requirement, for example, gas purification methods, such as a distillation method, an absorption method, an adsorption method, and a membrane separation method, are known. Regarding the distillation method, distillation must be repeated in multiple stages for separation if an impurity has a similar boiling point, for example, in the case of propylene and propane (a boiling point difference 4.9° C.). Thus, a large facility and the setting of precise distillation conditions are necessary, which are huge barriers to practical use (e.g., PTL 1). It is theoretically possible, but unpractical, to reach the target purity by increasing the number of stages of the distillation column.

Regarding an absorption method, it is necessary to set precise operating conditions because separation performance is greatly dependent on the selectivity of an absorption carrier (e.g., PTL 2). Further, a large heat source is necessary when dissipating. Thus, the absorption method is a technology requiring a large-scale facility. Furthermore, the amount of gas used in the field of semiconductors is small. Thus, this method is not suitable for the production of the small amount of gas used in the field of semiconductors, etc.

Various attempts have been made to utilize an adsorption method. However, due to low selectivity, it is difficult to selectively adsorb a target gas for the efficient production of a high purity gas of interest (e.g., Non-PTL 1).

A membrane separation method is more preferable than a distillation method, an absorption method, and an adsorption method from the viewpoint of selectivity, continuous productivity, energy savings, etc. In particular, according to the membrane separation method, a high purity gas can be supplied without edge cutting of piping, and thus, products of constant quality can be obtained in subsequent steps. The separation performance and the permeation performance of the gas separation membrane can be designed by the selection of a material such that a desired amount of a gas with a desired purity can be supplied. Further, according to the membrane separation method, it is possible to continuously supply a high purity gas in a single pass. Furthermore, unlike a distillation method and an absorption method, a heat source is not necessary, and thus, it is possible to reduce the space occupied by gas purification equipment.

CITATION LIST

Patent Literature

[PTL 1] WO 2015/141686
[PTL 2] US 2015/0025293
[PTL 3] WO 2009/093666
[PTL 4] Japanese Patent No. 4469635
[NPL 1] Propane/propylene separation by pressure swing adsorption: sorbent comparison and multiplicity of cyclic steady states, Salil U. Regel, Ralph T. Yang, Chemical Engineering Science, 2002, 57, 1139-1149.

SUMMARY

Technical Problem

There are various chemical resistant materials which can be used for the porous membrane and the housing of the membrane module for gas separation. However, the range of materials which can be used for the adhesive thereof is currently very narrow, because it is difficult to achieve the balance between the handleability during manufacturing and the performance or long-term stability of the membrane module for gas separation.

For example, if the durability of the adhesive is low, the peeling of the adhesive from the porous membrane or the housing could occur over time, the housing could be damaged by contraction and swelling of the adhesive, resulting in mixture of a purified gas and a raw material in the housing or leakage of a gas from the housing, the adhesive could deteriorate and dissolve, resulting in contamination inside the housing and contamination of a purified gas, and thus, the use for a long period of time would be difficult. In particular, when it is necessary for the purity of a purified gas to be high, the purified gas cannot satisfy this purity due to even slight deterioration of the adhesive, such that it is difficult to continuously use the membrane module for gas separation.

Conversely, if a highly durable adhesive is used, it is difficult to handle the adhesive during manufacturing. For example, fluorine-based thermoplastic resins, such as polytetrafluoroethylene (PTFE), are known to be excellent in chemical resistance. However, since PTFE has a high softening temperature, it is necessary to select a porous membrane having a sufficient durability at the softening temperature of PTFE when PTFE is used as the adhesive. Thus, a problem in the severe limitation of materials usable for the porous membrane would arise. Fluorine-based thermoplastic resins, such as polytetrafluoroethylene (PTFE), cannot be used as an adhesive for polyvinylidene fluoride (PVDF), polysulfone (PSU), polyethersulfone (PES), and polyethylene (PE), which are commonly used for porous membranes. Further, fluorine-based resins, such as PTFE, have a problem of high prices.

In particular, in consideration of the practical application of a gas separation membrane, the adhesive part is required to be a preferable form in view of both the material and the manufacturing method. Regarding gas separation, in particular, in the case of the separation of a hydrocarbon gas, such as an olefin, or in the case of a gas separation active layer containing a metal salt, the gas or the metal salt easily promotes the deterioration of the adhesive. Thus, it is difficult to conceive of and realize an adhesive which can achieve the balance between handleability during manufacturing and performance or long-term stability of the membrane module for gas separation.

From the above background, it has been difficult to provide a long-term practical membrane module for gas separation, specifically, a membrane module for gas separation of a hydrocarbon gas, in particular, a membrane module for gas separation, comprising a gas separation active layer containing a metal.

The present invention has been achieved in light of the above circumstances. The object thereof is to provide a long-term practical membrane module for gas separation, specifically, a membrane module for gas separation of a hydrocarbon gas.

Solution to Problem

The present inventors have conducted intensive studies to achieve the above object. As a result, the present inventors have found that, when a membrane module for gas separation having the following features is used, it is possible to provide a continuous gas supply system which occupies a reduced space and can continuously supply a required high purity gas, and it is possible to provide a membrane module unit which can effectively remove both inorganic impurities and organic impurities for a long period of time. In particular, the present invention encompasses the following aspects.

[1]
A membrane module for gas separation, comprising:
a housing;
a gas separation membrane disposed in the housing; and
an adhesive part for affixing the gas separation membrane to the housing, wherein
the gas separation membrane is composed of a porous membrane, and
the adhesive part satisfies at least one of the following (1) to (6):
1) the adhesive part has a low-mobility component having a composition ratio V (%), as measured by pulse NMR, wherein $30 \leq V \leq 100$;
2) the adhesive part has an attenuation rate W (%) represented by the following formula:

$$W=[(I1-I2)/I1] \times 100$$

wherein I1 is a signal intensity at start of measurement in the pulse NMR of the adhesive part, I2 is a signal intensity 0.05 msec after the measurement starts, and wherein $30 \leq W \leq 100$;
3) the adhesive part has a change ratio X (%) represented by the following formula:

$$X=[(V2-V1)/V1] \times 100$$

wherein V1 and V2 respectively represent the composition rates V(V1(%)) and V(V2(%)) before and after immersion of the adhesive part in a 7 mol/L aqueous silver nitrate solution or heptane for 1 month at 25° C., and wherein $-50 \leq X \leq 50$;

4) the adhesive part has a change ratio Y (%) represented by the following formula:

$$Y=[(W2-W1)/W1] \times 100$$

wherein W1 and W2 respectively represent the attenuation rates W(W1(%)) and W(W2(%)) before and after immersion of the adhesive part in a 7 mol/L aqueous silver nitrate solution or heptane for 1 month at 25° C., respectively, and wherein $-120 \leq Y \leq 120$;
5) the adhesive part has a nitrogen atom content ($C_N$, % by mass), wherein $0.0010 \leq C_N \leq 10$, and a sulfur atom content ($C_S$, % by mass), wherein $0.0010 \leq C_S \leq 0.01$; and
6) the adhesive part has a hardness K, wherein $10D \leq K \leq 90D$.
[2]
The membrane module for gas separation according to aspect 1, wherein the composition ratio V of the adhesive part is $50 \leq V \leq 100$.
[3]
The membrane module for gas separation according to aspect 2, wherein the composition ratio V of the adhesive part is $70 \leq V \leq 100$.
[4]
The membrane module for gas separation according to aspect 3, wherein the composition ratio V of the adhesive part is $90 \leq V \leq 100$.
[5]
The membrane module for gas separation according to any one of aspects 1 to 4, wherein the attenuation rate W of the adhesive part is $60 \leq W \leq 100$.
[6]
The membrane module for gas separation according to any one of aspects 1 to 5, wherein the attenuation rate W of the adhesive part is $90 \leq W \leq 100$.
[7]
The membrane module for gas separation according to any one of aspects 1 to 6, wherein the change ratio X of the adhesive part is $-25 \leq X \leq 25$.
[8]
The membrane module for gas separation according to any one of aspects 1 to 7, wherein the change ratio Y of the adhesive part is $-60 \leq Y \leq 60$.
[9]
The membrane module for gas separation according to any one of aspects 1 to 8, wherein the nitrogen atom content $C_N$ of the adhesive part is $0.0010 \leq C_N \leq 4.0$.
[10]
The membrane module for gas separation according to any one of aspects 1 to 9, wherein the nitrogen atom content $C_N$ of the adhesive part is $0.0010 \leq C_N \leq 0.30$.
[11]
The membrane module for gas separation according to any one of aspects 1 to 10, wherein the sulfur atom content $C_S$ of the adhesive part is $0.0010 \leq C_S \leq 0.0070$.
[12]
The membrane module for gas separation according to any one of aspects 1 to 11, wherein the hardness K of the adhesive part is $30D \leq K \leq 90D$.
[13]
The membrane module for gas separation according to any one of aspects 1 to 12, wherein the hardness K of the adhesive part is $50D \leq K \leq 90D$.
[14]
The membrane module for gas separation according to any one of aspects 1 to 13, wherein the adhesive part is a cured product of an adhesive, and a change ratio of a bending Young's modulus and a change ratio of a bending strength after and before immersion of the adhesive part in a 7 mol/L aqueous silver nitrate solution or heptane for 1 month at 25° C. are each within a range of −30% to +30%.

[15]
The membrane module for gas separation according to any one of aspects 1 to 14, wherein the adhesive part is a cured product of an adhesive, and a change in mass per surface area of the test piece after and before immersion of the adhesive part in a 7 mol/L aqueous silver nitrate solution or heptane for 1 month at 25° C. is within a range of −30 mg/cm$^2$ to +30 mg/cm$^2$.

[16]
The membrane module for gas separation according to any one of aspects 1 to 15, wherein the adhesive part is a cured product of an adhesive, and a change ratio of the thickness of the test piece after and before immersion of the adhesive part in a 7 mol/L aqueous silver nitrate solution or heptane for 1 month at 25° C. is within a range of −5% to +5%.

[17]
The membrane module for gas separation according to any one of aspects 1 to 16, wherein the adhesive part contains a cured product of an epoxy resin adhesive or a polyurethane resin adhesive.

[18]
The membrane module for gas separation according to any one of aspects 1 to 17, wherein the adhesive part does not substantially contain a cured product of a fluorine thermoplastic resin.

[19]
The membrane module for gas separation according to any one of aspects 1 to 18, wherein the gas separation membrane comprises a metal salt containing monovalent Ag and/or monovalent Cu.

[20]
The membrane module for gas separation according to any one of aspects 1 to 19, wherein a permeation rate of propylene gas is 10 GPU to 3,000 GPU and a separation factor of propylene/propane is 50 to 1,000, as measured using a mixed gas composed of 40% by mass of propane and 60% by mass of propylene with respect to the membrane module for gas separation at a supply side gas flow rate of 190 cc/min per 2 cm$^2$ membrane area and a permeation side gas flow rate of 50 cc/min per 2 cm$^2$ membrane area in a humidified atmosphere under isobaric conditions at 30° C.

[21]
A continuous gas supply system of a gas flow type, comprising:
a raw material gas inlet;
a raw-material-gas purification part for purifying a raw material gas to generate a purified gas;
and
a purified gas outlet, wherein
the purified gas has a purity of 99.5% by mass or higher, and
the raw-material-gas purification part is composed of a module selected from the group consisting of a module loaded with an adsorbent, a module loaded with an absorbent, and a membrane module for gas separation comprising a gas separation membrane.

[22]
The continuous gas supply system according to aspect 21, wherein the raw-gas purification part is composed of the membrane module for gas separation and the gas separation membrane is composed of a porous membrane.

[23]
A continuous gas supply system, wherein the continuous gas supply system is of a gas flow type and comprises a raw material gas inlet, a raw-gas purification part for purifying a raw material gas to generate a purified gas, and a purified gas outlet, and the raw-gas purification part is composed of the membrane module for gas separation according to any one of aspects 1 to 20.

[24]
The continuous gas supply system according to aspect 23, wherein the purified gas has a purity of 99.5% by mass or higher.

[25]
The continuous gas supply system according to any one of aspects 21 to 24, wherein the purified gas comprises a hydrocarbon gas as a main component.

[26]
The continuous gas supply system according to aspect 25, wherein the hydrocarbon gas is an olefin gas.

[27]
The continuous gas supply system according to aspect 26, wherein the olefin gas is ethylene or propylene.

[28]
The continuous gas supply system according to aspect 25, wherein the hydrocarbon gas is an aliphatic hydrocarbon having 1 to 4 carbon atoms.

[29]
The continuous gas supply system according to any one of aspects 21 to 28, wherein the purified gas contains non-hydrocarbon gases at a total amount of 5000 ppm or less.

[30]
The continuous gas supply system according to any one of aspects 21 to 28, wherein the purified gas contains a non-hydrocarbon gas and the non-hydrocarbon gas is one or more selected from the group consisting of oxygen, nitrogen, water, carbon monoxide, carbon dioxide, and hydrogen.

[31]
The continuous gas supply system according to aspect 30, wherein the non-hydrocarbon gas comprises water.

[32]
The continuous gas supply system according to any one of aspects 1 to 31, wherein the gas separation membrane is a composite membrane having a porous membrane and a gas separation active layer.

[33]
The continuous gas supply system according to any one of aspects 21 to 32, wherein a separation factor of propylene/propane is 50 to 100,000, as measured using a mixed gas composed of 40% by mass of propane and 60% by mass of propylene with respect to the membrane module for gas separation at a supply side gas flow rate of 190 cc/min per 2 cm$^2$ membrane area and a permeation side gas flow rate of 50 cc/min per 2 cm$^2$ membrane area in a humidified atmosphere under isobaric conditions at 30° C.

[34]
The continuous gas supply system according to any one of aspects 21 to 33, wherein the gas separation membrane has a porous membrane and a gas separation active layer disposed on the porous membrane,
an interface between the porous membrane and the gas separation active layer does not have a dense layer or has a dense layer which is approximately parallel to the interface and has a thickness of less than 1 μm and an average pore diameter of less than 0.01 μm,
A is 0.05 μm to 0.5 μm, and a ratio A/B is more than 0 to 0.9, wherein A is an average pore diameter in a depth range of the porous membrane ranging from the gas separation active layer to the depth of 2 μm and B is an average pore diameter in a depth range to the depth of 10 μm.

[35]
The continuous gas supply system according to any one of aspects 21 to 34, wherein the membrane module for gas separation comprises monovalent Ag and/or monovalent Cu.
[36]
A method for producing an olefin gas having a purity of 99.5% by mass or higher, comprising using the continuous gas supply system according to any one of aspects 21 to 35.
[37]
The method for producing an olefin gas according to aspect 36, wherein the olefin gas is propylene for CVD supply.
[38]
A membrane module unit comprising:
a membrane module for gas separation which comprises:
a housing,
a gas separation membrane disposed in the housing and composed of a porous membrane and gas separation active layer disposed on the porous membrane,
an adhesive part for affixing the gas separation membrane to the housing;
a humidifying mechanism for humidifying a raw material gas to be supplied to the gas separation membrane; and
a dehydrating mechanism for dehydrating a gas purified by the gas separation membrane.
[39]
The membrane module unit according to aspect 38, wherein an interface between the porous membrane and the gas separation active layer does not have a dense layer or has a dense layer which is approximately parallel to the interface and has a thickness of less than 1 μm and an average pore diameter of less than 0.01 μm,
A is 0.05 μm to 0.5 μm, and a ratio A/B is more than 0 to 0.9, wherein A is an average pore diameter in a depth range of the porous membrane ranging from the gas separation active layer to the depth of 2 μm and B is an average pore diameter in a depth range to the depth of 10 μm.
The membrane module unit according to aspect 38 or 39, configured to provide an olefin gas having a purity of 99.9% by mass or higher as a purified gas.
[41]
The membrane module unit according to any one of aspects 38 to 40, further comprising a gas purity detection system.
[42]
The membrane module unit according to any one of aspects 38 to 41, wherein the gas separation active layer is composed of a polymer containing one or more selected from the group consisting of an amino group, a pyridyl group, an imidazolyl group, an indolyl group, a hydroxyl group, a phenol group, an ether group, a carboxyl group, an ester group, an amide group, a carbonyl group, a thiol group, a thioether group, a sulfone group, a sulfonyl group, and a sulfonamide group.
[43]
The membrane module unit according to aspect 42, wherein the gas separation active layer is composed of a polymer containing one or more selected from the group consisting of an amino group, a sulfone group, and a hydroxyl group.
[44]
The membrane module unit according to aspect 42 or 43, wherein the polymer is a polyamine.
[45]
The membrane module unit according to aspect 44, wherein the polyamine is chitosan.
[46]
The membrane module unit according to any one of aspects 38 to 45, wherein the gas separation membrane contains monovalent Ag and/or monovalent Cu.

[47]
The membrane module unit according to any one of aspects 38 to 46, wherein the porous membrane contains a fluororesin.
[48]
The membrane module unit according to aspect 47, wherein the fluororesin is PVDF.
[49]
The membrane module unit according to any one of aspects 38 to 48, wherein a separation factor of propylene/propane is 50 to 100,000, as measured using a mixed gas composed of 40% by mass of propane and 60% by mass of propylene at a supply side gas flow rate of 190 cc/min per 2 cm$^2$ membrane area and a permeation side gas flow rate of 50 cc/min per 2 cm$^2$ membrane area in a humidified atmosphere under isobaric conditions at 30° C.
[50] A method for producing an olefin gas having a purity of 99.9% by mass or higher, comprising using the membrane module unit according to any one of aspects 38 to 49.
[51]
The method for producing an olefin gas according to aspect 50, wherein the olefin gas is propylene for CVD supply.

Advantageous Effects of Invention

According to the present invention, it is possible to provide a membrane module for gas separation which can maintain a permeation rate and a high separation performance in the separation of, in particular, a hydrocarbon gas, such as an olefin.

BRIEF DESCRIPTION OF DRAWINGS

FIG. 2 is a schematic cross-sectional view showing another example of the configuration of the membrane module for gas separation of the present embodiment.

DESCRIPTION OF EMBODIMENTS

Hereinafter, the present invention will be described in detail with reference to drawings as necessary, with a focus on the preferred embodiment (also referred to as "the present embodiment" in the present disclosure) of the present invention.

<Membrane Module for Gas Separation>

The membrane module for gas separation of the present embodiment comprises:
a housing;
a gas separation membrane disposed in the housing; and
an adhesive part for affixing the gas separation membrane to the housing, wherein
the gas separation membrane is composed of a porous membrane, and
the adhesive part satisfies at least one of the following (1) to (6):
1) the adhesive part has a low-mobility component having a composition ratio V (%), as measured by pulse NMR, wherein $30 \leq V \leq 100$;
2) the adhesive part has an attenuation rate W (%) represented by the following formula:

$$W=[(I1-I2)/I1] \times 100$$

wherein I1 is a signal intensity at start of measurement in the pulse NMR of the adhesive part, I2 is a signal intensity 0.05 msec after the measurement starts, and
wherein $30 \leq W \leq 100$;
3) the adhesive part has a change ratio X (%) represented by the following formula:

$$X=[(V2-V1)/V1] \times 100$$

wherein V1 and V2 respectively represent the composition rates V(V1(%)) and V(V2(%)) before and after immersion of the adhesive part in a 7 mol/L aqueous silver nitrate solution or heptane for 1 month at 25° C., and
wherein $-50 \leq X \leq 50$;
4) the adhesive part has a change ratio Y (%) represented by the following formula:

$$Y=[(W2-W1)/W1] \times 100$$

wherein W1 and W2 respectively represent the attenuation rates W(W1(%)) and W(W2(%)) before and after immersion of the adhesive part in a 7 mol/L aqueous silver nitrate solution or heptane for 1 month at 25° C., respectively, and
wherein $-120 \leq Y \leq 120$;
5) the adhesive part has a nitrogen atom content ($C_N$, % by mass), wherein $0.0010 \leq C_N \leq 10$, and a sulfur atom content ($C_S$, % by mass), wherein $0.0010 \leq C_S \leq 0.01$; and
6) the adhesive part has a hardness K, wherein $10D \leq K \leq 90D$.

The specific aspects as examples of the membrane module for gas separation of the present embodiment will be described below with reference to drawings.

Figure 1:
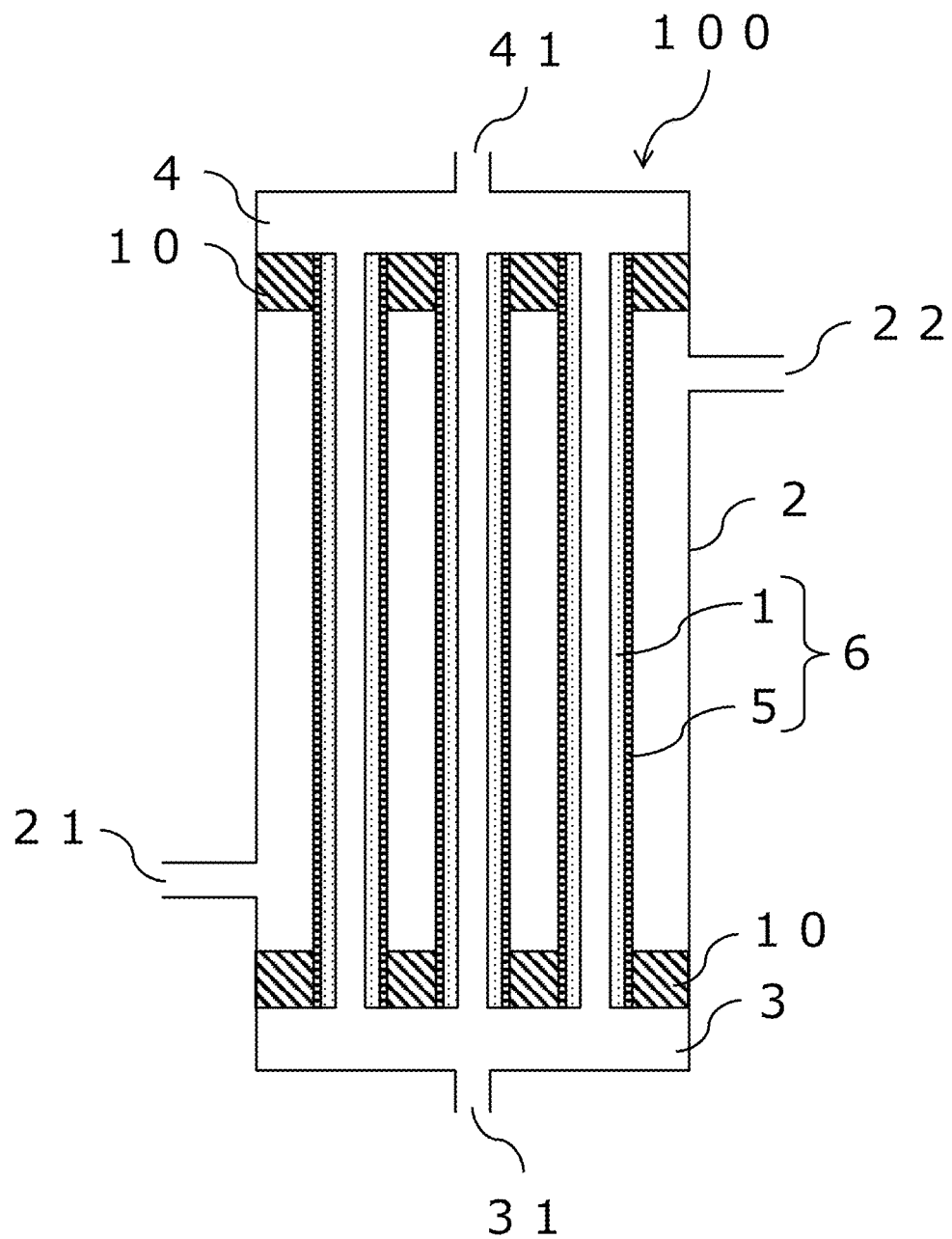
FIG. 1 is a schematic cross-sectional view showing an example of the configuration of the membrane module for gas separation of the present embodiment.

FIG. 1 and FIG. 2 depict examples of the configurations of the membrane module for gas separation of the present embodiment. FIG. 1 is a schematic cross-sectional view showing an example of the membrane module for gas separation which comprises a cylindrical housing and a hollow fiber gas separation membrane.

The membrane module 100 of FIG. 1 comprises:
a cylindrical housing 2 composed of a gas supply port 21 and a process gas outlet 22;
a hollow fiber gas separation membrane 6 housed in the cylindrical housing 2 and composed of a gas separation active layer 5 on the surface of a hollow fiber porous membrane 1; in which
the above gas separation membrane 6 is adhered and affixed to the housing 2 by an adhesive part 10, and
further comprises a footer part 3 having a permeable gas inlet 31 and a header part 4 having a separation gas outlet 41.

Neither of the ends of the gas separation membrane 6 are closed. The permeable gas inlet 31, the hollow portion of the gas separation membrane 6, and the separation gas outlet 41 are configured so that a fluid can flow. The fluid can also flow between a gas supply port 21 and a process gas outlet 22. The hollow portion of the gas separation membrane 6 and the external space of the gas separation membrane 6 are blocked except for the contact therebetween via the gas separation membrane.

In the membrane module 100 of FIG. 1, a gas to be separated (e.g., a mixture of an olefin and a paraffin) as raw material gas is introduced into the module from the gas supply port 21, and contacts the surface of the gas separation membrane 6. At this time, among components of the gas to be separated, a component (separation gas) having a high affinity with at least one of a porous membrane 1 and a gas separation active layer 5 is released into the space inside the gas separation membrane 6 through the outer wall of the gas separation membrane 6. Among components of the gas to be separated, a component (separation gas) having a low affinity with both the porous membrane 1 and the gas separation active layer 5 is released as a purified gas from the process gas outlet 22.

A permeation gas may be supplied from the permeable gas inlet 31 of the housing 2. As a function thereof, this permeation gas is released from the separation gas outlet 41 together with the component of the gas to be separated which is released into the space inside the gas separation membrane 6, whereby the collection of a separation gas is possible.

A gas which does not react with the housing 2, the adhesive part 4, the gas separation membrane 6, or the separation gas is suitable for the permeation gas. For example, an inert gas may be used. Examples of the inert gas include rare gases, such as helium and argon, and nitrogen.

FIG. 2 is a schematic cross-sectional view (FIG. 2(A) is a cross-sectional view and FIG. 2(B) is a longitudinal sectional view) showing an example of the membrane module for gas separation, in which the housing is cylindrical and the gas separation membrane is a flat sheet membrane.

The membrane module 200 of FIG. 2 comprises:
a cylindrical housing 2 composed of a permeable gas inlet 21, a separation gas outlet 22, a gas supply port 31, a process gas outlet 41, and a plate-like member 11 for affixing a gas separation membrane 6; in which
the gas separation membrane 6 is a flat sheet membrane composed of a flat sheet porous membrane 1 on one surface of a gas separation active layer 5 is housed in the cylindrical housing 2, and
the gas separation membrane 6 is adhered and affixed to the housing 2 by the adhesive part 10 via the plate-like member 11.

A space through which a fluid can flow is formed between the gas supply port 21 and the process gas outlet 22. This space is bounded by the surface of the gas separation membrane 6 on the side where the gas separation active layer 5 is present. A space through which a fluid can flow is formed between the permeable gas inlet 31 and the separation gas outlet 41. This space is bounded by the surface of the gas separation membrane 6 on the side where the gas separation active layer 5 is absent. The first space bounded by the surface of the gas separation membrane 6 on the side where the gas separation active layer 5 is present and the second space bounded by the surface of the gas separation membrane 6 on the side where the gas separation active layer 5 is absent are blocked except for the connection via the gas separation membrane therebetween.

In the membrane module 200 of FIG. 2, a gas to be separated is introduced into the first space of the module from the gas supply port 21, and contacts the surface of the gas separation membrane 6. Only a separation gas which has a high affinity with at least one of a porous membrane 1 and a gas separation active layer 5 is released into the second space through the gas separation membrane 6. Among components of the gas to be separated, a component which has a low affinity with both the porous membrane 1 and the gas separation active layer 5 is discharged from the process gas outlet 22 through the first space.

A permeation gas may be supplied from a permeable gas inlet 31 of the housing 2. This permeation gas is released from the separation gas outlet 41 together with the component of the gas to be separated which is released into the space inside the gas separation membrane 6.

The remaining aspects may be the same as those of the membrane module 100 of FIG. 1.

[Raw Material Gas]

The raw material gas of the present embodiment is a mixed gas of two or more gases including a gas component for the purpose of separation. Examples of the gas component for the purpose of separation include methane, ethane, ethylene, propane, propylene, butane, 1-butene, 2-butene, isobutane, isobutene, butadiene, monosilane, arsine, phosphine, diborane, germane, dichlorosilane, hydrogen selenide, silicon tetrachloride, disilane, boron trifluoride, boron trichloride, hydrogen chloride, ammonia, nitrogen trifluoride, silicon tetrafluoride, Freon-218, hydrogen bromide, chlorine, chlorine trifluoride, Freon-14, Freon-23, Freon-116, Freon-32, nitrous oxide, trichlorosilane, titanium tetrachloride, hydrogen fluoride, phosphorus trifluoride, phosphorus pentafluoride, tungsten hexafluoride, Freon-22, Freon-123, oxygen, nitrogen, water, carbon monoxide, carbon dioxide, and hydrogen. The raw material gas contains the gas component for the purpose of separation in an amount of 50% by mass or more, preferably 90% by mass or more, more preferably 95% by mass or more, even more preferably 98% by mass or more, and most preferably 99.5% by mass or more.

[Purified Gas]

The purified gas of the present embodiment is a gas containing the gas component for the purpose of separation in an amount of preferably 99.5% by mass or more, more preferably 99.9% by mass or more, even more preferably 99.99% by mass or more, and most preferably 99.999% by mass or more. Examples of the gas component for the purpose of separation include hydrocarbon gases. Examples of the hydrocarbon gases include paraffin gases such as methane, ethane, propane, butane, isobutene, and olefin gases, such as ethylene, propylene, 1-butene, 2-butene, isobutene, and butadiene. In the exemplified aspects, the hydrocarbon gas is an aliphatic hydrocarbon having 1 to 4 carbon atoms.

In a typical aspect, the main component of the purified gas is a hydrocarbon gas. "Main component" as used herein refers to a gas contained in the largest amount (on a mass basis) in the purified gas.

In one aspect, the above hydrocarbon gas is an olefin gas. In one aspect, the olefin gas is ethylene or propylene.

"Hydrocarbon gas" as used herein refers to a gas having both a carbon atom and a hydrogen atom in a molecule. "Paraffin gas" as used herein refers to a gas which does not have a C-C unsaturated bond in a molecule.

Examples of non-hydrocarbon gases include monosilane, monosilane, arsine, phosphine, diborane, germane, dichlorosilane, hydrogen selenide, silicon tetrachloride, disilane, boron trifluoride, boron trichloride, hydrogen chloride, ammonia, nitrogen trifluoride, silicon tetrafluoride, Freon-218, hydrogen bromide, chlorine, chlorine trifluoride, Freon-14, Freon-23, Freon-116, Freon-32, nitrous oxide, trichlorosilane, titanium tetrachloride, hydrogen fluoride, phosphorous trifluoride, phosphorus pentafluoride, tungsten hexafluoride, Freon-22, Freon-123, oxygen, nitrogen, water, carbon monoxide, carbon dioxide, and hydrogen. "Non-hydrocarbon gas" as used herein refers to a gas which does not contain either or both of a carbon atom and a hydrogen atom in a molecule. In one aspect, the non-hydrocarbon gas is one or more selected from the group consisting of oxygen, nitrogen, water, carbon monoxide, carbon dioxide, and hydrogen. In one aspect, the non-hydrocarbon gas is water.

The concentration of a gas component other than the component for the purpose of separation in the purified gas is preferably 5000 ppm by mass or less, more preferably 1000 ppm by mass or less, even more preferably 100 ppm by mass or less, and most preferably 10 ppm by mass or less. From the viewpoint of increasing the yield in a process using the purified gas, the lower the concentration of the gas component other than the component for the purpose of separation, the better. However, adjusting the concentration to substantially zero is not preferable from the viewpoint of safety, etc.

Since a hydrocarbon gas containing, for example, an olefin gas is combustible gas, it has a potential problem of ignition or explosion. In order to reduce the risk of ignition or explosion and improve safety, it is necessary to remove one of a combustible material, a burnable material, and an ignition source. Therefore, when water is contained in addition to the hydrocarbon gas, which is the gas for the purpose of separation, an effect on the suppression of the generation of static electricity as an ignition source can be expected. It is only necessary that the gas component other than the component for the purpose of separation be substantially different from the gas for the purpose of the separation. In a typical aspect, the gas component other than the component for the purpose of separation is a non-hydrocarbon gas.

[Adhesive Part]

The adhesive part of the membrane module for gas separation of the present embodiment has a function of adhering and affixing the gas separation membrane to the housing in aspects in which a gas supplied to the module can pass through the gas separation membrane.

In general, adhesive parts of membrane modules for gas separation could be deteriorated by the gas to be separated (in particular, hydrocarbon gases) and a metal optionally added to a gas separation active layer (in particular, metal salts). However, the adhesive part of the membrane module for gas separation of the present embodiment has high resistance to the gases to be separated and metals because the adhesive part satisfies at least one of the following (1) to (6):

1) the adhesive part has a low-mobility component having a composition ratio V (%), as measured by pulse NMR, wherein $30 \leq V \leq 100$;

2) the adhesive part has an attenuation rate W (%) represented by the following formula:

$$W = [(I1 - I2)/I1] \times 100$$

wherein I1 is a signal intensity at start of measurement in the pulse NMR of the adhesive part, I2 is a signal intensity 0.05 msec after the measurement starts, and
wherein 30≤W≤100;
3) the adhesive part has a change ratio X (%) represented by the following formula:

$$X=[(V2-V1)/V1]\times 100$$

wherein V1 and V2 respectively represent the composition rates V(V1(%)) and V(V2(%)) before and after immersion of the adhesive part in a 7 mol/L aqueous silver nitrate solution or heptane for 1 month at 25° C., and
wherein −50≤X≤50;
4) the adhesive part has a change ratio Y (%) represented by the following formula:

$$Y=[(W2-W1)/W1]\times 100$$

wherein W1 and W2 respectively represent the attenuation rates W(W1(%)) and W(W2(%)) before and after immersion of the adhesive part in a 7 mol/L aqueous silver nitrate solution or heptane for 1 month at 25° C., respectively, and
wherein −120≤Y≤120;
5) the adhesive part has a nitrogen atom content ($C_N$, % by mass), wherein 0.0010≤$C_N$≤10, and a sulfur atom content ($C_S$, % by mass), wherein 0.0010≤$C_S$≤0.01; and
6) the adhesive part has a hardness K, wherein 10D≤K≤90D.

In the present embodiment, the "low-mobility component" of the adhesive part refers to a component represented by a Lorentz function in pulse NMR measurement, as will be described below. The low-mobility component is, for example, a crystalline component or a component in a glass state. The present inventors have focused on the following: Commercially available adhesives commonly used in the art have a composition ratio of a low-mobility component of less than 30% and an attenuation rate of signal intensity of less than 30%. The composition ratio and attenuation rate each could result in swelling by a hydrocarbon gas or invasion of a metal salt. As a result, during the use of the membrane module, the adhesive part could become swollen or eluted, causing peeling of the adhesive part from the gas separation membrane, collapse of the adhesive part, or destruction of the housing, whereby the raw material gas (gas to be separated) could become mixed with the purified gas (separation gas or process gas).

In one aspect of the present embodiment, it is advantageous to adjust the composition ratio V of the low-mobility component in the adhesive part and/or the attenuation rate W of the signal intensity to 30% or more, in terms of avoiding the above problem. The higher the above composition ratio V and attenuation rate W, the better.

In another aspect of the present embodiment, it is advantageous that a change ratio X of the composition ratio V and/or a change ratio Y of the attenuation rate W after immersion of the adhesive part in an aqueous silver nitrate solution or heptane be within predetermined ranges, in terms of the satisfactory durability of the adhesive part.

In one aspect, the composition ratio (V) of the low-mobility component calculated in the pulse NMR is preferably 30% to 100%, more preferably 50% to 100%, even more preferably 70% to 100%, and most preferably 90% to 100%. The attenuation rate (W) of the signal intensity (I2) 0.05 msec after the start of measurement to the signal intensity (I1) at the start of measurement calculated in the above pulse NMR is preferably 30% to 100%, more preferably 60% to 100%, and even more preferably 90% to 100%. When V and/or W satisfy the above values, an adhesive part has high resistance to gases to be separated and metals, and thus, a highly practical membrane module for gas separation can be provided.

In another aspect of the present embodiment, the adhesive part of the membrane module for gas separation satisfies at least one of, and preferably both of, the following 3) and 4):
3) the above change ratio X (%) after immersion of the adhesive part in a 7 mol/L aqueous silver nitrate solution or heptane is in the range of −50% to 50%, and preferably −25% to 25%; and
4) the above change ratio Y (%) after immersion of the adhesive part in a 7 mol/L aqueous silver nitrate solution or heptane is in the range of −120% to 120%, and preferably −60% to 60%. When the change ratio X and/or the change ratio Y satisfy the above values, the adhesive part has high resistance to gases to be separated and metals, and thus, a highly practical membrane module for gas separation can be provided. In a preferred aspect, both of the above change ratio X and change ratio Y after immersion of the adhesive part in a 7 mol/L aqueous silver nitrate solution or heptane are within the above ranges.

In the present embodiment, the composition ratio (V, %) of the low-mobility component obtained from pulse NMR can be calculated by the following method. The measurement is performed using a Minispec MQ20 available from Bruker Biosipn, Inc., as the measurement device for pulse NMR, with 1H as a measuring nuclide, and a solid echo method as the measurement method with a cumulative number of 256. Specifically, a glass tube having an outer diameter of 10 mm and containing a measurement sample cut to a height of 1.5 cm is placed within the device, which is controlled at a temperature of 190° C. Five minutes after the placement, the relaxation time T2 of 1H is measured by a solid echo method. The repeated standby time during the measurement is set to be not less than 5 times larger than the relaxation time T1 of the sample. Fitting of the thus-obtained magnetization decay curve (curve showing time-dependent change in magnetization intensity) is carried out using formula I consisting of a Weibull function and a Lorenz function:

[Math. 1]

$$MT(t)=C_s\exp(-(1/W_a)(t/T_s)^{Wa})+C_l\exp(-t/T_l) \quad (1)$$

The low-mobility component is the component represented using a Weibull function. The high-mobility component is the component represented using a Lorenz function.

In the above formula, M(t) represents the signal intensity at a certain time t, Cs and Cl represent composition ratios (%) of the low-mobility component and the high-mobility component, Wa represents a Weibull coefficient, and Ts and Tl represent the relaxation times of the low-mobility component and the high-mobility component. Fitting is performed using the initial value of the Weibull coefficient of 2.0 such that the Weibull coefficient is 1.2 to 2.0. The composition ratio V (%) of the low-mobility component of the present embodiment is the composition ratio (%) of the low-mobility component with respect to the total of low-mobility component and the high-mobility component in the above formula.

According to the above procedures, from the magnetization decay curve obtained using pulse NMR, the attenuation rate (W, %) of signal intensity at 0.05 msec can be calculated using the signal intensity at the start of measurement at the time of acquisition start as 100%.

The method for obtaining the adhesive part of the present embodiment, in which the composition ratio V and/or the attenuation rate W satisfy the above values, is not limited.

However, a preferable means is the optimization of the manufacturing method of the adhesive part. It is generally difficult to make V and/or W satisfy the above values when, for example, the adhesive part of the membrane module is manufactured using a polyurethane resin adhesive or an epoxy adhesive, which are commonly used in the art, by a method which is commonly carried out in the art. For example, polyurethane resin adhesives usually comprise a base resin composed of a hydroxyl group-containing compound and a curing agent composed of an isocyanate compound. Epoxy adhesives usually comprise a base resin composed of an epoxy group-containing compound and a curing agent. The mixing ratio of the base resin and the curing agent and the heating time and rate at the time of curing are not carefully reviewed in many cases. Thus, a membrane module for gas separation with sufficient long-term stability cannot easily be obtained simply using an adhesive commonly used for membrane modules.

In the present invention, it has been found that, regarding high temperature curing adhesives, which have not been used as adhesives for membrane modules for gas separation, controlling the mixing ratio of the base resin and the curing agent, as well as the heating time and rate at the time of curing is advantageous for the manufacturing of an adhesive part in which V and/or W satisfy the above values. It has been further found that, regarding room temperature curing- and mid-temperature curing adhesives, controlling the mixing ratio of the base resin and the curing agent as well as the heating time and rate, and using a plurality of compounds as the base resin and/or the curing agent are advantageous for the manufacturing of an adhesive in which V and/or W satisfy the above values. According such means, the structure (degree of crosslinking, etc.) of a product is controlled, and thus desired V and/or W can be achieved.

In another aspect of the present embodiment, the adhesive part of the membrane module for gas separation satisfies:
5) the adhesive part has a nitrogen atom content ($C_N$, % by mass), wherein $0.0010 \leq C_N \leq 10$, and a sulfur atom content ($C_S$, % by mass), wherein $0.0010 \leq C_S \leq 0.01$.

In general, adhesive parts of membrane modules for gas separation could be deteriorated by a gas to be separated (in particular, hydrocarbon gases) and a metal optionally added to a gas separation active layer (in particular, metal salts). However, the adhesive part, in which the nitrogen atom content ($C_N$, % by mass) is $0.0010 \leq C_N \leq 10$, and the sulfur atom content ($C_S$, % by mass) is $0.0010 \leq C_S \leq 0.01$, has high resistance to the gases to be separated and metals.

The nitrogen atoms and sulfur atoms in the above adhesive part are considered to be derived from at least one of the curing agent and additive of the adhesive. Commercially available adhesives commonly used in the art usually contain about 10% by mass or more of nitrogen atoms and about 0.12% by mass or more of sulfur atoms. These nitrogen atoms and sulfur atoms cooperate with the metal salt, which could result in collapse of the adhesive part, and subsequently, damage to the housing. Thus, the lower each of the nitrogen atom content $C_N$ and sulfur atom content $C_S$ of the adhesive par, the better.

However, according to the findings of the present inventors, when the value of $C_N$ is excessively decreased, there is a limit to an increase in durability with the decrease in $C_N$. To prevent an excessive increase in production cost of the membrane module for gas separation of the present embodiment, there is little practical benefit of decreasing the value of $C_N$ to less than 0.0010%.

It is considered that the degradation activity of sulfur atoms in the adhesive part is much larger than that of nitrogen atoms. Thus, the lower the sulfur atom content $C_S$ of the adhesive part, the better. However, according to the findings of the present inventors, when the value of $C_S$ is excessively decreased, there is a limit to an increase in durability with the decrease in $C_S$. To prevent an excessive increase in production cost of the membrane module for gas separation of the present embodiment, there is little practical benefit of decreasing the value of $C_S$ to less than 0.0010%.

The above nitrogen atom content ($C_N$) is preferably 0.0010% by mass to 4.0% by mass, and particularly preferably 0.0010% by mass to 0.30% by mass. The above sulfur atom content ($C_S$) is preferably 0.0010% by mass to 0.0070% by mass. An adhesive part in which $C_N$ and $C_S$ are the above values has high resistance to gases to be separated and metals, and thus, a highly practical membrane module for gas separation can be provided.

In the membrane module for gas separation of the present embodiment, the ratio ($C_N/C_S$) of the nitrogen atom content ($C_N$) to the sulfur atom content ($C_S$) of the adhesive part is preferably 30 to 1,600. When this ratio $C_N/C_S$ is 30 or more, the resistance to gases to be separated and metals is satisfactory because intensive attack on this part can be suppressed by making the sulfur atom content of the adhesive part relatively low. When this ratio ($C_N/C_S$) is 1,600 or less, the resistance to gases to be separated and metals is satisfactory. The ratio ($C_N/C_S$) is more preferably 400 or less, 200 or less, or 100 or less, from the viewpoint of imparting higher durability.

It is not necessary to limit the adhesive part to specific materials as long as the nitrogen atom content ($C_N$) and the sulfur atom content ($C_S$) of the adhesive part or the ration ($C_N/C_S$) can satisfy the above value. Adhesive parts, in which the above values are satisfied, can be obtained by optimizing the manufacturing method thereof. In order to achieve the above $C_N$, $C_S$ and $C_N/C_S$, for example, an acid anhydride epoxy resin which is not commonly used in the art can be used for the adhesive part. Acid anhydride epoxy resins are high temperature curing resins, and thus, when these resins are used for adhesive parts, problems occur, such as cracks due to thermal contraction at the time of manufacture and deterioration of the mechanical strength of these resins due to abnormal heat generation. However, in the present embodiment, the mixing ratio of the base resin and the curing agent, the heating time and rate at the time of curing, etc., have been reviewed, and it has been found that acid anhydride epoxy resins can be used as the adhesive parts of membrane modules for gas separation, and as a result, the above $C_N$, $C_S$, and $C_N/C_S$ can be achieved.

Further, regarding polyurethane resin adhesives originally having a high nitrogen atom content ($C_N$) and a high sulfur atom content ($C_S$), the above $C_N$, $C_S$, and $C_N/C_S$ can be achieved by combining the polyurethane resin adhesives with other adhesives to form the adhesive parts, adjusting the mixing ratio of the base resin and the curing agent, and mixing a plurality of base resins and a curing agent.

In the present embodiment, the nitrogen atom content ($C_N$) of the adhesive part can be calculated by analyzing a sample of the adhesive part collected from the membrane module for gas separation by a CHN coder (carbon, hydrogen, and nitrogen simultaneous determination device) method. The sulfur atom content ($C_S$) of the adhesive part can be calculated by analyzing a sample of the adhesive part collected from the membrane module for gas separation by an ion chromatogram method.

In another aspect of the present embodiment, the adhesive part of the membrane module for gas separation has a hardness K of $10D \leq K \leq 90D$ (the measurement method of hardness conforms to JIS K 6253 and ISO 7619, and the same applies hereinafter in the present specification). Such an adhesive part has a high durability against gases to be separated and metals. When the hardness K satisfies the above value, mechanical strength is satisfactory, and the affixed state of the porous membrane and the adhesive part can be satisfactorily maintained for a long period of time. In one aspect, the above hardness K is 10D≤K≤90D, preferably 30D≤K≤90D, and more preferably 50D≤K≤90D. When the hardness K is 10D or more, mechanical strength is satisfactory and the affixed state of the adhesive part and the housing is satisfactory, whereby the likelihood of the mixture of a raw material gas with a purified gas in the housing or gas leakage to the outside of the module can be reduced. Further, when the hardness K is 90D or less, it is possible to avoid the following problem; in operation, the adhesive part rubs against the porous membrane, and defects occur on the porous membrane or the gas separation active layer, whereby it is difficult to continuously use the membrane module for gas separation.

It is not necessary to limit the adhesive part to specific materials as long as the hardness K of the adhesive part can satisfy the above value. Adhesive parts in which the above values are satisfied can be obtained by optimizing the manufacturing method thereof. For example, when polyurethane resin adhesives and epoxy adhesives, which are commonly used in the art, are simply cured by a room temperature curing method, which is a common method in the art, satisfaction of the above value tends to be difficult. The method for satisfying the above value may be heat curing. However, a rapid temperature rise may cause abnormal reduction of the mechanical strength of the adhesive part due to cracking of the adhesive part and abnormal heat generation. In the present embodiment, it has been found that adhesive parts used for large-volume modules can satisfy the above value by curing stepwise, slowly raising the temperature, heating for a long period of time without excessively raising the temperature, etc.

Further, high temperature curing adhesives, which are seldom used in the art due to the difficulty in handling at the time of manufacturing have hardnesses K which can satisfy the above value. Due to high temperature curing, it is difficult to cure a large volume thereof. However, in the present embodiment, the mixing ratio of the base resin and the curing agent, the heating time and rate at the time of curing, etc., have been reviewed, and it has been found that the hardness K can satisfy the above value and high temperature curing adhesives can be used as the adhesive parts of membrane modules for gas separation.

In an aspect in which the adhesive part is a cured product of an adhesive, the adhesive part is preferably formed using an adhesive having at least one of the following properties (1) to (3), more preferably formed using an adhesive having at least two of the following properties (1) to (3), and particularly preferably having all of the following properties (1) to (3).

(1) A change ratio of a bending Young's modulus and a change ratio of a bending strength of a test piece of the adhesive part after and before immersion of the test piece in a 7 mol/L aqueous silver nitrate solution or heptane for 1 month at 25° C. are each within a range of −30% to +30%.
(2) A change in mass per surface area of a test piece of the adhesive part after and before immersion of the test piece in a 7 mol/L aqueous silver nitrate solution or heptane for 1 month at 25° C. is within a range of −30 mg/cm$^2$ to +30 mg/cm$^2$.

(3) A change ratio of the thickness of a test piece of the adhesive part after and before immersion of the test piece in a 7 mol/L aqueous silver nitrate solution or heptane for 1 month at 25° C. is within a range of −5% to +5%.

An adhesive part in which the change ratio of the bending Young's modulus and the change ratio of the bending strength after immersion of the adhesive part in a 7 mol/L aqueous silver nitrate solution or heptane are less than −30% or more than +30% could cause swelling, elution, or degradation during use of the membrane module. When degradation of the adhesive part occurs, there is a risk that peeling of the adhesive part from the gas separation membrane, collapse of the adhesive part, destruction of the housing, or the like could occur, and a raw material gas (gas to be separated) could becine mixed with a purified gas (separation gas or process gas). In order to provide a highly practical membrane module for gas separation, an adhesive part in which the change ratio of the bending Young's modulus and the change ratio of the bending strength are each −30% to +30% is preferably used, and an adhesive part in which the ratios are each −10% to +10% is more preferably used.

An adhesive part in which the change in mass per surface area after immersion of the adhesive part in a 7 mol/L aqueous silver nitrate solution or heptane is more than +30 mg/cm$^2$ could cause swelling during use of the membrane module. When swelling of the adhesive part occurs, there is a risk that peeling of the adhesive part from the gas separation membrane, collapse of the adhesive part, destruction of the housing, or the like occurs. An adhesive part made from an adhesive in which the change in mass per surface area after immersion is less than −30 mg/cm$^2$ could elute during use of the membrane module. When the adhesive part elutes, there is a risk that it is difficult to strictly partition the raw material gas and the purified gas. In order to provide a highly practical membrane module for gas separation, an adhesive part in which the change in mass per surface area is −30 mg/cm$^2$ to +30 mg/cm$^2$ is preferably used, and an adhesive part in which the change in mass per surface area is −10 mg/cm$^2$ to +10 mg/cm$^2$ is more preferably used.

An adhesive part in which the thickness change after immersion of the adhesive part in a 7 mol/L aqueous silver nitrate solution or heptane is more than +5% could cause swelling during use of the membrane module. An adhesive part made from an adhesive in which the change in mass per surface area after immersion is less than −5% could elute during use of the membrane module. In order to provide a highly practical membrane module for gas separation, an adhesive part in which the thickness change is −5% to +5% is preferably used, and an adhesive part in which the thickness change is −2% to +2% is more preferably used.

The adhesive part of the membrane module for gas separation of the present embodiment preferably contains one or more selected from a cured product of an epoxy resin adhesive and a cured product of a polyurethane resin adhesive.

The above epoxy resin adhesive contains a base resin comprising an epoxy group-containing compound and a curing agent. The adhesive part of the membrane module of the present embodiment can be formed by curing this adhesive. This epoxy resin adhesive may further contain a curing accelerator in addition to the base resin and the curing agent.

The above polyurethane resin adhesive contains a base resin comprising a hydroxyl group-containing compound and a curing agent comprising an isocyanate compound. The adhesive part of the membrane module of the present embodiment can be formed by curing this adhesive.

Examples of an epoxy group-containing compound, which is the base resin of the epoxy resin adhesives, include bisphenol epoxy resins such as a bisphenol A epoxy resins and bisphenol F epoxy resins; and novolac epoxy resins, trisphenolmethane epoxy resins, naphthalene epoxy resins, phenoxy epoxy resins, alicyclic epoxy resins, glycidyl amine epoxy resins, and glycidyl ester epoxy resins. Thereamong, bisphenol epoxy resins are preferable from the viewpoint of suppressing the swelling and degradation due to a gas to be separated or a metal salt. A mixture of these resins may be used.

Examples of the curing agent for the epoxy resin adhesive include amines, polyamino amides, phenols, and acid anhydrides. Thereamong, acid anhydrides are preferably used, because cured products of epoxy resin adhesives obtained using an acid anhydride as the curing agent have strong interaction between molecular chains, and thus, swelling and degradation due to a gas to be separated and a metal salt are unlikely to occur. When an acid anhydride is used as the curing agent, an adhesive part of the resulting membrane module for gas separation contains an acid anhydride epoxy resin.

Examples of the acid anhydride used as the curing agent for the epoxy resin adhesives include aromatic anhydrides, such as phthalic anhydride, trimellitic anhydride, pyromellitic anhydride, benzophenonetetracarboxylic anhydride, ethylene glycol bistrimellitate, and glycerol tris trimellitate; aliphatic acid anhydrides, such as methyl-5-norbornene-2, 3-dicarboxylic anhydride (methyl nadic anhydride), dodecenyl succinic anhydride, polyadipic anhydride, polyazelaic acid anhydride, polysebacic anhydride, poly(ethyloctadecanedioic acid) anhydride, poly (phenylhexadecanoic acid) anhydride; and
alicyclic acid anhydrides, such as methyltetrahydrophthalic anhydride, methylhexahydrophthalic anhydride, methylheumic anhydride, hexahydrophthalic anhydride, trialkyltetrahydrophthalic anhydride, and methylcyclohexene dicarboxylic anhydride. These acid anhydrides may be used solely or in mixture thereof.

Examples of a curing accelerator, which is optionally used for the epoxy resin adhesive, include conventionally used compounds, such as tertiary amines (e.g., tris(dimethylaminomethyl)phenol, 1,8-diazabicyclo[5,4,0]undecene-7 (DBU), 1,5-diazabicyclo[4.3.0]nonene-5 (DBN), and 1,4-diazabicyclo[2.2.2]octane (DABCO)), imidazoles, Lewis acids, and Bronsted acids. These compounds may be used solely or in mixture thereof.

The types of base resin and curing agent used for an epoxy resin adhesive can be confirmed by measuring the adhesive part of a membrane module by, for example, infrared spectroscopy (IR), pyrolysis GC/IR, pyrolysis GC/MS, elemental analysis, time-of-flight secondary ion mass spectrometry (TOF-SIMS), solid nuclear magnetic resonance analysis (solid state NMR), or X-ray photoelectron spectroscopy (XPS).

From the viewpoint of the durability of the produced membrane modules for gas separation, an alicyclic epoxy resin, a bisphenol A epoxy resin, or a naphthalene epoxy is preferably used as the base resin, and an alicyclic acid anhydride epoxy is preferably used as the curing agent.

Examples of a hydroxyl group-containing compound used as the base resin of a urethane resin adhesive include hydrocarbon polyols, such as polyester polyols, polyether polyols, polycarbonate polyols, polybutadiene glycols, polyacrylic polyols, and polyisoprene polyols, and compounds mainly composed of castor oil-based polyols. Thereamong, polyacrylic polyols and castor oil-based polyols have strong interaction between molecular chains, and thus, swelling and degradation due to a gas to be separated and a metal salt are unlikely to occur. These compounds may be used solely or in mixture thereof.

Examples of an isocyanate compound, which is the curing agent of the polyurethane resin adhesive include, aromatic polyisocyanates, such as 4,4'-diphenylmethane diisocyanate (hereinafter, referred to as MDI), polymethylene polyphenylene polyisocyanate; aliphatic polyisocyanates, such as hexamethylene diisocyanate; alicyclic polyisocyanates, such as isophorone diisocyanate and 4,4'-methylenebis (cyclohexane isocyanate); and compounds mainly composed thereof. Thereamong, aliphatic polyisocyanates, such as hexamethylene diisocyanate are preferable from the viewpoints of having strong interaction between molecular chains, and thus and suppressing the swelling and degradation due to a gas to be separated or a metal salt. A mixture of these resins may be used.

In the above urethane formation reaction, a catalyst commonly used for urethane formation reactions may be optionally used to accelerate the reaction. Examples of the catalyst include amine catalysts (triethylamine, N-ethylmorpholine, and triethylenediamine, and the cycloamidines described in U.S. Pat. No. 4,524,104, such as 1,8-diaza-bicyclo[5.4.0]-7-undecene ("DBU" available from San-Apro Ltd)), tin-based catalysts (dibutyltin dilaurate, dioctyltin dilaurate, and tin octylate), titanium-based catalysts (tetrabutyl titanate, etc.), and bismuth-based catalysts (bismuth trioctylate etc.). These compounds may be used solely or in mixture thereof.

The stabilizer is not particularly limited, and may be a publicly known antioxidant and/or an ultraviolet absorber. The stabilizer is usually used in an amount of 0 to 5% by weight, preferably 0.1 to 3% by weight, based on the weight of the polyurethane resin.

Examples of the antioxidant include phenol antioxidants (2,6-di-t-butyl-p-cresol and butylated hydroxyanisole etc.), bisphenol antioxidants (2,2'-methylenebis (4-methyl-6-t-butylphenol), etc.), and phosphorus antioxidants (triphenyl phosphite, diphenyl isodecyl phosphite, etc.).

Examples of the ultraviolet absorber include benzophenone ultraviolet absorbers (2,4-dihydroxybenzophenone, 2-hydroxy-4-methoxybenzophenone, etc.), benzotriazole ultraviolet absorbers (2-(2'-hydroxy-5'-methylphenyl)benzotriazole, etc.), salicylic acid ultraviolet absorbers (phenyl salicylate, etc.), hindered amine ultraviolet absorbers (bis(2, 2,6,6-tetramethyl-4-piperidyl)sebacate).

Examples of other additives include an antifusion agent and a flame retardant.

The types of base resin and curing agent used for the polyurethane resin can be confirmed by measuring the adhesive part of the membrane module by, for example, infrared spectroscopy (IR), pyrolysis GC/IR, pyrolysis GC/MS, elemental analysis, time-of-flight secondary ion mass spectrometry (TOF-SIMS), solid nuclear magnetic resonance analysis (solid state NMR), or X-ray photoelectron spectroscopy (XPS).

It is preferable that the adhesive part of the membrane module for gas separation of the present embodiment be substantially free of a cured product of a fluorine thermoplastic resin. The phrase "not substantially contain" as used herein means that the mass ratio of the cured product of a fluorine thermoplastic resin in the adhesive part is 5% by mass or less, preferably 3% by mass or less, more preferably 1% by mass or less, and further preferably 0.1% by mass or less.

Examples of the fluorine thermoplastic resin of the present embodiment include polytetrafluoroethylene (PTFE), tetrafluoroethylene/perfluoroalkylvinylether copolymers (PFA), tetrafluoroethylene/hexafluoropropylene copolymers (FEP), tetrafluoroethylene/ethylene copolymers (ETFE), polyvinylidene fluoride (PVDF), polychlorotrifluoroethylene (PCTFE), and chlorotrifluoroethylene/ethylene copolymers (ECTFE).

The adhesive used in the present embodiment (thus, the adhesive part of the membrane module for gas separation used in the present embodiment) may optionally further contain various additives, such as a filler, an aging retardant, and a reinforcing agent.

[Gas Separation Membrane]

The gas separation membrane of the membrane module for gas separation of the present embodiment has a porous membrane. This gas separation membrane may have a gas separation active layer on the porous membrane, and may contain a metal salt containing monovalent Ag or monovalent Cu. When the gas separation membrane contains a metal salt containing monovalent Ag or monovalent Cu, the metal salt is preferably present in the gas separation active layer.

Figure 3:
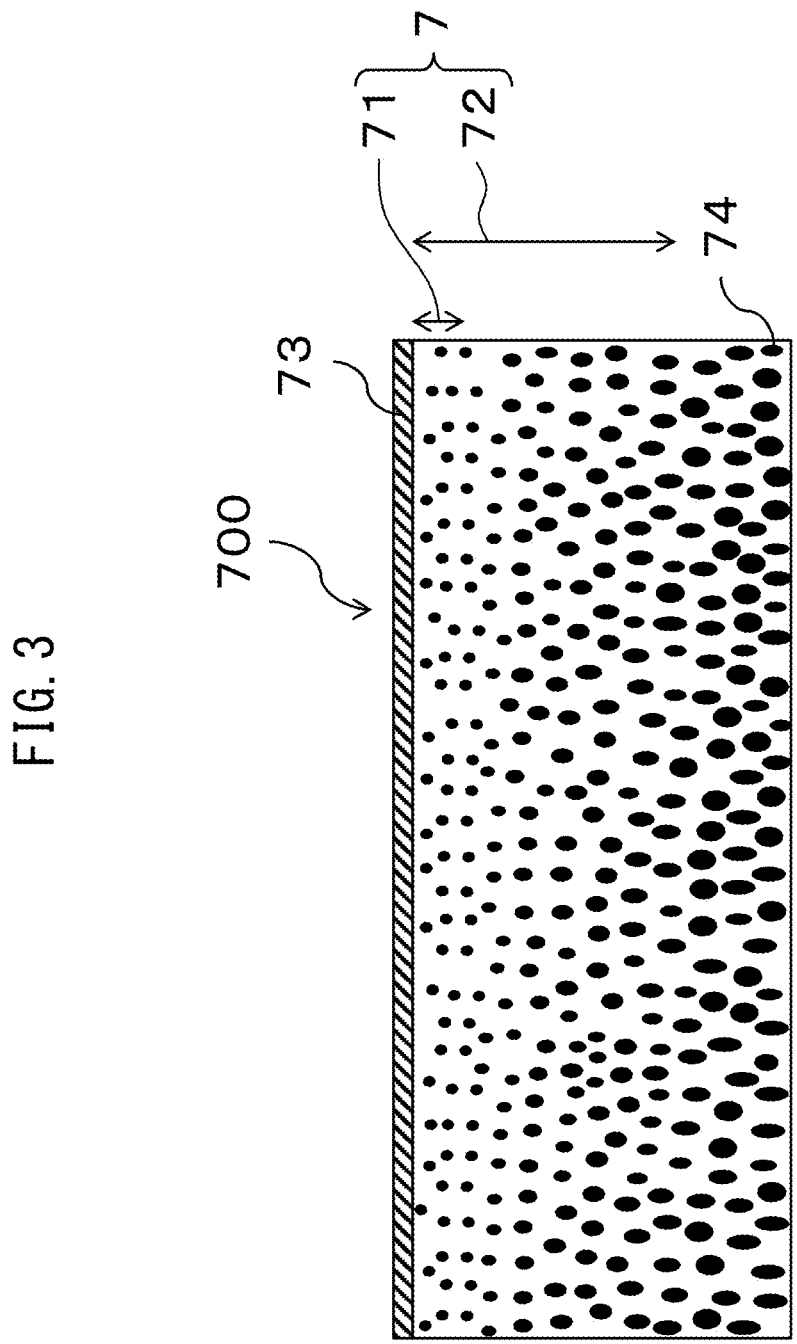
FIG. 3 is a schematic drawing for explaining the separation membrane of the present embodiment.

Refer to, for example, FIG. 3. The gas separation membrane 700 of the present embodiment has a porous membrane 7 (which has a large number of pores 74) and a gas separation active layer 73 disposed on the porous membrane 7. A dense layer having an average pore diameter of less than 0.01 µm is absent at the interface between the porous membrane 7 and the gas separation active layer 73 or a dense layer having a thickness of less than 1 µm and parallel to the interface is present. When A is the average pore diameter in a depth range 71 of the porous membrane 7 ranging from the gas separation active layer 73 to a depth of 2 µm and B is the average pore diameter in a depth range 72 to the depth of 10 µm, A is preferably 0.05 µm or more from the viewpoint of obtaining a satisfactory gas permeation rate and preferably 0.5 µm or less from the viewpoint of obtaining a satisfactory separation performance. Further, the ratio A/B is more than 0 and is preferably 0.9 or less from the viewpoint of obtaining a satisfactory separation performance. From the viewpoint of porous membrane, it is preferable that the gas separation membrane have a relatively small average pore diameter in a region close to the gas separation active layer side (e.g., the above depth range 71).

(Porous Membrane)

In a gas separation membrane used in a system composed of a humidifying mechanism, water could penetrate into the porous membrane, resulting in a liquid sealed state in which water blocks the pores, and in a significantly decreased gas permeation rate. As the pore size of the porous membrane decreases, the time for the liquid sealed state decreases, gas permeability decreases, and separation selectivity decreases. Thus, in the porous membrane of the gas separation membrane of the present embodiment, a dense layer having a small pore diameter is absent at the interface with a gas separation active layer, or if present, it is preferable the dense layer be approximately parallel to the interface and have a thickness of less than 1 µm. The above dense layer has an average pore diameter of less than 0.01 µm. A dense layer is absent on the surface of the porous membrane on the side where the gas separation active layer is present, or if present, the dense layer has a thickness of less than 1 µm, whereby the thickness of the liquid sealed layer can be reduced and a high gas permeation rate can be maintained.

The dense layer may be present at the interface between the porous membrane and the gas separation active layer. Further, the dense layer may be present inside the porous membrane or on a surface on the side opposite to the gas separation active layer. If present, the dense layer preferably has a thickness of less than 1 µm.

The thickness of the dense layer can be determined by, for example, a transmission electron microscope (TEM) or an X-ray photoelectron spectroscope equipped with a gas cluster ion beam gun (GCIB-XPS) in combination with a scanning electron microscope (SEM). Specifically, the thickness can be determined by, for example, the following procedures.

(i) The membrane thickness of the gas separation active layer is measured.

When TEM is used

When TEM is used, for example, under the following conditions, the membrane thickness of the gas separation active layer is evaluated.

(Pre-Treatment)

The gas separation membrane is, for example, frozen and crushed to form a measurement sample. The outer surface of the sample is subjected to Pt coating and the sample is embedded in an epoxy resin. The sample is cut by an ultramicrotome (e.g., manufactured by LEICA, Type "UC-6") to form an ultra-thin section. Phosphotungstic acid staining is performed to form a microsection sample.

(Measurement)

Measurement can be carried out using, for example, a TEM of Type "5-5500" available from Hitachi at an acceleration voltage: 30 kV.

When GCIB-XPS is used

When GCIB-XPS is used, the membrane thickness of the gas separation active layer can be obtained from the resulting distribution curve of relative element concentration.

GCIB-XPS can be carried out using, for example, Type "Versa Probe II" available from Ulvac-phi Inc., under the following conditions.

(GCIB conditions)

Acceleration voltage: 15 kV

Cluster size: $Ar_{2500}$

Cluster range: 3 mm×3 mm

Rotation of sample during etching: Yes

Etching interval: 3 minutes/level

Sample current: 23 nA

Total etching time: 69 min (XPS conditions)

X-ray: 15 kV, 25 W

Beam size: 100 m (ii) The thickness of the dense layer is evaluated.

The thickness of the dense layer can be evaluated from the membrane thickness of the gas separation active layer determined above in (i), and an SEM image. SEM evaluation is carried out under, for example, the following conditions.

(Pretreatment)

The gas separation membrane is frozen and crushed in a plane approximately perpendicular to the interface between the porous membrane and the gas separation active layer to form a measurement sample. The outer surface of the sample is subjected to Pt coating to form a microsection sample.

(Measurement)

Measurement can be carried out using, for example, an SEM of the type "Carry Scope (JCM-5100)" available from JEOL at an acceleration voltage: 20 kV.

On the observation screen with a magnification of 10,000 times, pore sizes other than the pore size of the gas separation active layer determined in (i) are observed to determine the thickness of a layer comprising pores of less than 0.01 µm.

In the present embodiment, when A is the average pore diameter in a range of the porous membrane ranging from the interface between the porous membrane and the gas separation active layer to a depth of 2 μm in the vertical direction and B is the average pore diameter in a range to a depth of 10 μm, it is preferable that A be 0.05 μm to 0.5 μm and the ratio A/B be more than 0 to 0.9. The larger the pore diameter of the porous membrane, the better in terms of the prevention of the liquid sealed state. However, when the pore diameter exceeds 0.5 m, it becomes difficult to form a gas separation active layer without defects. The average pore diameter A is 0.05 μm or more, whereby the liquid sealed state can be prevented and a high gas permeation rate can be maintained. The average pore diameter A is preferably 0.1 μm or more, and more preferably 0.3 μm or more from the viewpoint of the prevention of the liquid sealed state. The average pore diameter A is 0.5 μm or less, whereby a gas separation active layer without defects can be formed. The average pore diameter B is preferably 0.06 μm to 5 μm, more preferably 0.1 μm to 3 μm, even more preferably 0.5 μm to 1 μm, from the same viewpoint as for the average pore diameter A, i.e., the viewpoint of achieving both the prevention of the liquid sealed state and the formation of the gas separation active layer without defects.

Further, the average pore diameter ratio A/B is 0.9 or less, whereby both the prevention of liquid sealing and defect-free coatability of the gas separation active layer can be achieved. In order to achieve both the prevention of liquid sealing and defect-free coatability of the gas separation active layer and obtain a high gas permeation rate and a high permeation selectivity, A/B is preferably 0.6, and more preferably 0.4 or less.

The average pore diameters A and B can be determined by, for example, the following evaluation.
(i) Like the measurement of the dense layer described above, a measurement sample is a cross section approximately vertical to the interface between the porous membrane and the gas separation active layer. A boundary part between the porous membrane and the gas separation active layer is measured by SEM at an acceleration voltage of 20 kV and a magnification of 10,000 times.
(ii) The average pore diameter A in a range (numeral 71 of FIG. 3) of the porous membrane ranging from the interface between the porous membrane and the gas separation active layer to the depth of 2 μm is calculated. In the range from the interface to the depth of 2 m, five lines are drawn at substantially equal intervals in each of the longitudinal direction and the lateral direction at the right angle. The lengths of the lines crossing the pores shown in a photo are measured. An arithmetic mean value of these measured values is obtained. This is the average pore diameter. In order to increase the accuracy of the pore diameter measurement, it is preferable that the number of holes traversed by 10 lines in total in the longitudinal and lateral directions be 20 or more. When the gas separation active layer partly penetrates into the porous membrane, the average pore diameter is measured on the basis of the interface between a part of a hollow fiber membrane where the gas separation active layer does not penetrate and a part of the hollow fiber membrane where the gas separation active layer penetrates.
(iii) The average pore diameter B in a range (numeral 72 of FIG. 3) of the porous membrane ranging from the interface between the porous membrane and the gas separation active layer to the depth of 10 μm is calculated. This calculation of the average pore diameter B can be carried out by the same procedures as those described above in (ii) except for the measurement range.

The material of the porous membrane is not particularly limited as long as the material has a sufficient corrosion resistance to a raw material gas and a sufficient durability at the operation temperature and the operation pressure. However, organic materials are preferably used. Examples of the organic material for forming the porous membrane include homopolymers and copolymers of polyethersulfone, polyvinylidene fluoride (PVDF), polytetrafluoroethylene (PTFE), polyimide, polybenzoxazole, and polybenzimidazole. Thereamong, polymers made from one or mixture thereof can be preferably used. In particular, fluorine-based resins have a high durability in a hydrocarbon atmosphere, and the processability of the obtained porous membranes is satisfactory. From this viewpoint, PVDF is most preferred.

The shape of the porous membrane may be a flat sheet membrane form, a hollow fiber form, or a pleated form. When the porous membrane is a hollow fiber, the inner diameter is appropriately determined in accordance with the throughput of raw material gas. The inner diameter of the hollow fiber support is generally selected in the range of 0.1 mm to 20 mm. In order to enhance the contact with the target gas contained in the raw material gas, it is preferable that the inner diameter of the hollow fiber support be 0.2 mm to 15 mm. The outer diameter of the hollow fiber support is not particularly limited, and is appropriately determined in consideration of the inner diameter of the hollow fiber support from the viewpoint of securing a thickness sufficient to withstand the pressure difference between the inside and the outside of the hollow fiber.

(Gas Separation Active Layer)

In the membrane module for gas separation of the present embodiment, the gas separation active layer is disposed on the above porous membrane to enhance gas separation performance.

The gas separation active layer preferably comprises a gas-selective polymer containing, in a repeating unit in its molecule, at least one of an amino group, a pyridyl group a group having an imidazole skeleton, a group having an indole skeleton, a hydroxyl group, a hydroxyphenyl group, a group having an ether structure, a carboxyl group, a group having an ester structure, an amide group, a carbonyl group, a thiol group, a group having a thioether structure, a sulfonyl group, a sulfonamide group, etc. The gas separation active layer has a repeating unit containing such a group, whereby a metal (in particular, metal salt) optionally contained in the gas separation active layer can be dispersed in a high concentration, and thus, the resulting gas separation membrane can be suitably used for the separation of, for example, an olefin and a paraffin.

The presence or absence of a functional group can be confirmed by elemental analysis, time-of-flight secondary ion mass spectrometry (TOF-SIMS), solid nuclear magnetic resonance analysis (solid state NMR), X-ray photoelectron spectroscopy (XPS), and the like.

The gas separation active layer preferably comprises a polymer having at least a repeating unit containing an amino group and more preferably comprises a polyamine. This is because the amino group of a polyamine has relatively weak interaction with a metal (in particular, metal salt) optionally contained the gas separation active layer, whereby the a decrease in interaction between the metal and the gas to be separated (in particular, an olefin) can be prevented. The presence of an amino group in the gas separation active layer can be confirmed by, for example, infrared spectroscopic analysis.

The polyamine is preferably a gel-like polymer and more preferably a crystalline polymer, because polyamines which are crystalline polymers can homogenously disperse a metal (in particular, a metal salt) optionally contained in the gas separation active layer in a high concentration, whereby satisfactory durability can be imparted to the gas separation membrane.

Such a polyamine may be a chitosan. "Chitosan" as used herein refers to compounds having repeating units comprising β-1,4-N-glucosamine and β-1,4-N-acetylglucosamine, in which the ratio of the β-1,4-N-glucosamine is 70% by mol or more.

A polyamine may be chemically modified with a functional group. The functional group is preferably at least one selected from the group consisting of, for example, an imidazolyl group, an isobutyl group, and a glyceryl group.

The number average molecular weight of the polyamine is preferably 100,000 to 3,000,000, and more preferably 300,000 to 1,500,000 from the viewpoint of improving the balance of the gas separation performance and the permeability. This number average molecular weight is a value obtained from the measurement by size exclusion chromatography using pullulan as a reference substance.

The presence of a chitosan in the gas separation active layer can be confirmed by, for example, time-of-flight secondary ion mass spectrometry (TOF-SIMS), or an X-ray photoelectron spectroscope equipped with an argon gas cluster ion gun (GCIB-XPS).

In the membrane module for gas separation of the present embodiment, the gas separation active layer may be a substance compatible with the gas to be separated (in particular, an olefin). In such a case, the resulting gas separation membrane can be used for the separation of, for example, an olefin and a paraffin.

The substance compatible with an olefin may be, for example, a metal salt. This metal salt is preferably a metal salt containing a metal ion selected from the group consisting of monovalent silver ($Ag^+$) and monovalent copper ($Cu^+$) or a complex ion thereof. More preferably, the metal salt is composed of a metal salt of $Ag^+$, $Cu^+$, or a complex ion thereof and an anion selected from the group consisting of $F^-$, $Cl^-$, $Br^-$, $I^-$, $CN^-$, $NO_3^-$, $SCN^-$, $ClO_4^-$, $CF_3SO_3^-$, $BF_4^-$, and $PF_6^-$.

The concentration of the metal salt of the gas separation active layer is preferably 10% by mass to 70% by mass, more preferably 30% by mass to 70% by mass, and even more preferably 50% by mass to 70% by mass. If the concentration of the metal salt is too low, a highly practical gas separation performance cannot be obtained. If the concentration of the metal salt is too high, there are disadvantages, such as high cost of the production of the membrane module for gas separation. Thus, the above concentration is preferable in consideration of the balance therebetween.

A gas separation active layer may be on either or both of the surfaces of the porous membrane.

When the gas separation membrane is a hollow fiber, the gas separation active layer may be present on only the outer surface, only the inner surface, or both of the outer surface and the inner surface of the hollow fiber.

[Housing]

The membrane module for gas separation of the present embodiment comprises a housing. This housing may have any structure and shape as long as the housing can house at least a gas separation membrane. For example, a cylindrical shape, a box shape, and other shapes are possible.

The housing preferably has a gas inlet and a gas outlet for the flow of a gas in a space to which the front surface side of the porous membrane belongs and a space to which the back-surface side of the porous membrane belongs, respectively, in which the spaces are separated by an adhesive layer.

Any material can be selected and used to form the housing without lamination as long as the material has a sufficient corrosion resistance to a gas to be separated and a sufficient durability at the operation temperature and the operation pressure. Examples of the material include metals and synthetic resins.

The size of the housing can be appropriately determined in accordance with the size of gas separation membrane to be housed in the housing, and the processing power of the gas separation.

<Performance of the Membrane Module for Gas Separation>

The above membrane module for gas separation of the present embodiment is suitably used for the separation of, for example, an olefin and a paraffin. Specifically, for example, the permeation rate of a propylene gas as measured using a mixed gas consisting of 40% by mass of propane and 60% by mass of propylene at the supply side gas flow rate of 190 cc/min per 2 $cm^2$ membrane area and a permeation side gas flow rate of 50 cc/min per 2 $cm^2$ membrane area in a humidified atmosphere under isobaric conditions at 30° C. is preferably 10 GPU to 3,000 GPU, more preferably 50 GPU to 2,000 GPU, even more preferably 100 GPU to 2,000 GPU. The separation factor of propylene/propane is preferably 50 to 1,000, more preferably 100 to 1,000, even more preferably 150 to 1,000.

These values are measured at a partial pressure of propylene of 1 atm or less, specifically, 0.6 atm.

<Method for the Production of the Membrane Module for Gas Separation>

The method for the production of the membrane module for gas separation of the present embodiment is:
a method for the production of the membrane module for gas separation comprising affixing a gas separation membrane having a porous membrane to the inside a housing with an adhesive, wherein the membrane module for gas separation satisfies at least one of the following (1) to (6):

1) the adhesive part has a low-mobility component having a composition ratio V (%), as measured by pulse NMR, wherein $30 \leq V \leq 100$;

2) the adhesive part has an attenuation rate W (%) represented by the following formula:

$$W=[(I1-I2)/I1] \times 100$$

wherein I1 is a signal intensity at start of measurement in the pulse NMR of the adhesive part, I2 is a signal intensity 0.05 msec after the measurement starts, and
wherein $30 \leq W \leq 100$;

3) the adhesive part has a change ratio X (%) represented by the following formula:

$$X=[(V2-V1)/V1] \times 100$$

wherein V1 and V2 respectively represent the composition rates V(V1(%)) and V(V2(%)) before and after immersion of the adhesive part in a 7 mol/L aqueous silver nitrate solution or heptane for 1 month at 25° C., and
wherein $-50 \leq X \leq 50$;

4) the adhesive part has a change ratio Y (%) represented by the following formula:

$$Y=[(W2-W1)/W1] \times 100$$

wherein W1 and W2 respectively represent the attenuation rates W(W1(%)) and W(W2(%)) before and after immersion of the adhesive part in a 7 mol/L aqueous silver nitrate solution or heptane for 1 month at 25° C., respectively, and wherein $-120 \leq Y \leq 120$;

5) the adhesive part has a nitrogen atom content ($C_N$, % by mass), wherein $0.0010 \leq C_N \leq 10$, and a sulfur atom content ($C_S$, % by mass), wherein $0.0010 \leq C_S \leq 0.01$; and 6) the adhesive part has a hardness K, wherein $10D \leq K \leq 90D$.

The method for the production of the membrane module for gas separation of the present embodiment will be described below in detail using an embodiment comprising a hollow fiber gas separation membrane as an example.

The method for production of the membrane module for gas separation of the present embodiment comprises the following:

a production step of producing a porous membrane;

a coating solution-producing step of producing a coating solution comprising an aqueous solution containing a gas selectivity polymer for forming a gas separation active layer;

a coating step of coating the surface of the above porous membrane with the above coating solution; and a step of producing an adhesive part, which is a cured product of an adhesive, by immersing a part of the porous membrane in the adhesive followed by curing the adhesive.

Prior to the coating step, an immersion step of immersing the porous membrane in a viscous aqueous solution may be included.

A drying step of drying the coated porous membrane to remove a solvent in the coating solution may be carried out.

[Production Step of Producing a Porous Membrane]

First, a method for the production of the porous membrane preferably used for the present embodiment is described.

The porous membrane can be obtained by nonsolvent-induced phase separation or thermally induced phase separation.

The production of a hollow fiber membrane of PVDF by nonsolvent induced phase separation will be explained below.

First, PVDF is dissolved in a solvent to prepare a PVDF solution. The molecular weight of the PVDF used in the present embodiment is preferably 2,000 to 100,000, and more preferably 10,000 to 50,000, as the number average molecular weight in terms of polystyrene as measured by size exclusion chromatography. This is because, if the molecular weight is too low, highly practical durability is not exhibited and other problems could arise, and conversely, if the molecular weight is too high, the production of the porous membrane is difficult, and other problems could arise.

In the present embodiment, the concentration of PVDF in the above PVDF solution is preferably 15% by mass to 50% by mass, and more preferably 20% by mass to 35% by mass. This is because, if the concentration of PVDF is too low, highly practical durability is not exhibited and other problems could arise, and conversely, if the concentration of PVDF is too high, the production of the porous membrane is difficult, and other problems could arise.

Examples of the solvent of the PVDF solution include good solvents, such as N-methyl-2-pyrrolidone, dimethylacetamide, dimethylformamide, dimethylsulfoxide; and poor solvents such as glycerin, ethylene glycol, triethylene glycol, polyethylene glycol, a nonionic surfactant. The mass ratio of the good solvent/the poor solvent in the PVDF solution is preferably 97/3 to 40/60 in consideration of an improvement in stability of the PVDF solution when used as a spinning solution, ease of obtaining a homogeneous membrane structure, etc.

Subsequently, spinning is carried out using the resulting PVDF solution as a spinning solution. The PVDF solution is discharged from the outer slit of a double tubular nozzle and a core liquid is discharged from the center hole. The core liquid may be water or a mixed solution of water and a good solvent.

The discharge rate of the core liquid is preferably 0.1 to 10 times, and more preferably 0.2 to 8 times the discharge rate of the PVDF solution. The discharge rates of the core liquid and the PVDF solution as the spinning solution are appropriately controlled within the above range, whereby a porous membrane having a preferable shape can be produced.

The spinning solution discharged from the nozzle passes through an aerially traveling part, thereafter is immersed in a coagulation bath to perform coagulation and phase separation, whereby a hollow fiber membrane is formed. As a coagulating liquid in the coagulation bath, for example, water can be used.

The hollow fiber membrane in a wet state removed from the coagulation bath is washed in a washing tank to remove the solvent and the like, and is thereafter dried with a drier.

As described above, a hollow fiber porous membrane can be obtained.

The porous membrane of the present embodiment may be selected from commercially available porous membranes having the predetermined parameters of the present embodiment.

[Impregnation Step]

The thus-obtained porous membrane may be directly subjected to the subsequent coating step or may be subjected to an impregnation step of impregnating the porous membrane with a viscous aqueous solution followed by the coating step.

The viscosity of the viscous aqueous solution of the present embodiment is preferably 1 cP to 200 cP, more preferably 5 cP to 150 cP, and even more preferably 10 cP to 100 cP. This is because, if the viscosity of viscous aqueous solution is less than 1 cP, the effects of the use of the viscous aqueous solution cannot be exhibited and other problems could arise, and conversely, if the viscosity of viscous aqueous solution is more than 200 cP, the porous membrane cannot be sufficiently impregnated with the viscous aqueous solution and other problems could arise.

The solute of the viscous aqueous solution of the present embodiment may be a substance which can be mixed with water at any ratio. For example, a glycol or a glycol ether is preferably used. Examples of the glycol include glycerin, ethylene glycol, diethylene glycol, and triethylene glycol, propylene glycol, dipropylene glycol, tripropylene glycol, polyethylene glycol. Examples of the glycol ether include ethylene glycol monomethyl ether, ethylene glycol monoethyl ether, ethylene glycol monobutyl ether, ethylene glycol isopropyl ether, ethylene glycol dimethyl ether, 3-methyl 3-methoxybutanol, ethylene glycol t-butyl ether, 3-methyl 3-methoxybutanol, 3-methoxy butanol, diethylene glycol monomethyl ether, diethylene glycol monobutyl ether, triethylene glycol monomethyl ether, triethylene glycol monobutyl ether, propylene glycol monomethyl ether, propylene glycol propyl ether, dipropylene glycol monomethyl ether, tripropylene glycol monomethyl ether. One or more selected from glycerin, ethylene glycol, and propylene glycol are preferably used. These solutes may be used solely or in a mixture thereof.

The concentration of a solute in the viscous aqueous solution is preferably 10% by mass to 90% by mass, and more preferably 20% by mass to 80% by mass. The solute is mixed with water within this range and the viscosity is adjusted to within the above range, whereby a viscous aqueous solution can be prepared.

The pH of the viscous aqueous solution is preferably 4 to 10, and more preferably 5 to 9. This is because if the pH of the viscous aqueous solution is too low or too high, the porous membrane cannot be impregnated with the viscous aqueous solution.

The immersion temperature at which the porous membrane is immersed in the viscous aqueous solution is preferably 0° C. to 100° C., and more preferably 20° C. to 80° C. This is because if the immersion temperature is lower than 0° C., the porous membrane cannot be sufficiently impregnated with the viscous aqueous solution and other problems could arise, and conversely, if the immersion temperature is higher than 100° C., the solvent (water) in the viscous aqueous solution excessively volatilizes during immersion and other problems could arise.

The immerse time is preferably 15 min to 5 h, and more preferably 30 min to 3 h. This is because if the immersion time is less than 15 min, the porous membrane cannot be sufficiently impregnated with the viscous aqueous solution and other problems could arise, and conversely, if the immersion time is more than 5 h, the production efficiency of the gas separation membrane could decrease and other problems could arise.

[Coating Solution-Producing Step]

The gas separation active layer can be formed by contacting the porous membrane with a coating solution. Examples of the contact method include a dip coating method (immersion method), a doctor-blade coating method, a gravure-coating method, a die-coating method, and a spray-coating method.

The formation of the gas separation active layer by contacting a chitosan therewith by a dip-coating method will be explained below.

First, a chitosan coating solution is prepared. A chitosan is dissolved in an aqueous solvent to form the chitosan coating solution. The concentration of the chitosan is preferably 0.2% by mass to 10% by mass, and more preferably 0.5% by mass to 5% by mass. If the concentration of the chitosan is less than 0.2% by mass, a highly practical gas separation membrane cannot be obtained. The chitosan used in the present embodiment may be chemically modified.

The chitosan coating solution may contain 80% by mass or less of an organic solvent with respect to the total solvent amount. Examples of the organic solvent include alcohols such as methanol, ethanol and propanol, polar solvents such as acetonitrile, acetone, dioxane, and tetrahydrofuran, etc. These organic solvents may be used solely or in a combination of two or more.

The chitosan coating solution may contain 10% by mass or less of a surfactant with respect to the total amount of the solution to improve wettability to the porous membrane. The surfactant is preferably a nonionic surfactant from the viewpoint of preventing electrostatic repulsion with the material forming the gas separation active layer, homogenously dissolving in any acidic, neutral, or basic aqueous solution, etc.

Examples of the nonionic surfactant include long chain fatty acid esters of polyoxyethylene and fluorine surfactants with perfluoro groups. Specific examples of the long chain fatty acid esters of polyoxyethylene include Tween 20 (polyoxyethylene sorbitan monolaurate), Tween 40 (Polyoxyethylene sorbitan monopalmitate), Tween 60 (polyoxyethylene sorbitan monostearate), Tween 80 (polyoxyethylene sorbitan monooleate) (which are available from Tokyo Chemical Industry Co., Ltd.), Triton-X100, Pluronic-F68, and Pluronic-F127. Specific examples of the fluorine surfactants with perfluoro groups include fluorine-based surfactant FC-4430 and FC-4432 (which are available from 3M), S-241, S-242, and S-243 (which are available from AGC Seimi Chemical Co., Ltd.), and F-444 and F-477 (which are available from DIC).

20% by mass or less of a viscous solute with respect to the total amount of the solution may be added to the chitosan coating solution to improve the flexibility of the gas separation active layer. The viscous solute is preferably a glycol, a glycol ether, or the like. Examples of the glycol include glycerin, ethylene glycol, diethylene glycol, triethylene glycol, propylene glycol, dipropylene glycol, tripropylene glycol, and polyethylene glycol. Examples of the glycol ether include ethylene glycol monomethyl ether, ethylene glycol monoethyl ether, ethylene glycol monobutyl ether, ethylene glycol isopropyl ether, ethylene glycol dimethyl ether, methyl 3-methoxybutanol, ethylene glycol t-butyl ether, 3-methyl 3-methoxybutanol, 3-methoxybutanol, diethylene glycol monomethyl ether, diethylene glycol monobutyl ether, triethylene glycol monomethyl ether, triethylene glycol monobutyl ether, propylene glycol monomethyl ether, propylene glycol propyl ether, dipropylene glycol monomethyl ether, and tripropylene glycol monomethyl ether. One or more selected from glycerin, ethylene glycol, and propylene glycol are preferred. These solutes may be used solely or in a combination of two or more.

[Coating Step]

The temperature of the coating solution when contacting the porous membrane is preferably 0° C. to 100° C., and more preferably 20° C. to 80° C. If the contact temperature is lower than 0° C., the porous membrane cannot be uniformly coated with the coating solution and other problems could arise. Conversely, if the contact temperature is higher than 100° C., the solvent (e.g., water) of the coating solution could excessively volatilize during contact and other problems could arise.

When contact is carried out by the immersion method, the contact time (immersion time) is preferably 15 min to 5 h, and more preferably 30 min to 3 h. If the contact time is less than 15 min, the porous membrane cannot be sufficiently coated and other problems could arise. Conversely, the contact time is more than 5 h, the production efficiency of the gas separation membrane could decrease and other problems could arise.

[Drying Step]

Subsequent to the above coating step, a drying step (solvent-removing step) may be optionally carried out. This drying step can be carried out by a method comprising allowing the coated porous membrane to stand in, for example, an environment of preferably 80° C. to 160° C., and more preferably 120° C. to 160° C. for preferably 5 min to 5 h, and more preferably 10 min to 3 h. This is because if the drying temperature is too low (less than 80° C.) and/or if the drying time is too short (less than 5 min), the solvent cannot be sufficiently removed by drying and other problems could arise, and conversely, if the drying temperature is too high (higher than 160° C.) and/or if the drying time is too long (more than 5 h), the production cost could increase, the production efficiency could decrease, and other problems could arise.

[Method for the Production of the Gas Separation Membrane Having a Gas Separation Active Layer Containing a Metal Salt]

The gas separation membrane having a gas separation active layer containing a metal salt can be produced by further contacting the thus-obtained gas separation membrane with an aqueous metal salt solution containing a desired metal salt. Thereafter, a drying step may be optionally carried out.

The concentration of metal salt of the above aqueous metal salt solution is preferably 0.1 mol/L to 50 mol/L. If the concentration of metal salt of the above aqueous metal salt solution is less than 0.1 mol/L, the resulting gas separation membrane, when used for the separation of an olefin and a paraffin, could not exhibit a highly practical separation performance. If the concentration is more than 50 mol/L, the cost of raw materials could increase and other problems could arise.

The contact treatment of the gas separation membrane with the aqueous metal salt solution is preferably carried out by an immersion method. The temperature of the aqueous solution at the time of immersion is preferably 10° C. to 90° C., and more preferably 20° C. to 80° C. If this immersion temperature is lower than 10° C., the gas separation active layer cannot be sufficiently impregnated with the metal salt and other problems could arise. Conversely, if the immersion temperature is higher than 90° C., the solvent (water) of the aqueous metal salt solution could excessively volatilize during immersion and other problems could arise.

Under the above production conditions, the gas separation membrane of the present embodiment can be produced.

In the membrane module for gas separation of the present embodiment, only one hollow fiber gas separation membrane may be used or a plurality thereof may be used together. When a plurality thereof are used together, the number thereof is preferably 10 to 100,000, and more preferably 10,000 to 50,000. When the number is 10 or more, the productivity of the membrane module for gas separation is high. The structure and the shape of the hollow fiber bundles can be appropriately designed in accordance with the application.

[Adhesive Part-Producing Step]

The thus-produced hollow fiber or hollow fiber bundle is housed in the housing. Thereafter, a predetermined amount of an adhesive is injected into both ends of the fiber or fiber bundle, and an adhesive part is formed by curing. The adhesive may be, for example, a two-part adhesive (e.g., the above epoxy resin adhesive or polyurethane resin adhesive).

First, a base resin and a curing agent are mixed and defoamed. The mixing weight ratio of the base resin to the curing agent (base resin/curing agent) is preferably 30/70 to 70/30, more preferably 40/60 to 60/40, and even more preferably 45/55 to 55/45. This is because if one of the ratios of the base resin and the curing agent is too low, poor curing or abnormal heat generation during curing occurs. Further, since the base resin or the curing agent volatilizes, it is desirable to determine the ratio in view of the curing temperature and the heating rate. Each of the base resin and the curing agent may be a mixture of a plurality of types.

Next, the mixed solution of the mixed and deformed base resin and curing agent is injected into the ends of a fiber or a fiber bundle and is heated. The mixed solution is cured by heating to form a cured part. This cured part is inferred to have a structure (e.g., crosslinked) which is durable during use over time of the membrane module for gas separation membrane. A single injection may be carried out or a plurality of injections of divided portions may be carried out. Abnormal heat generation during curing can be suppressed by the plurality of injections of divided portions. Further, in order to avoid abnormal heat generation, the cured part may be divided by partition boards.

The mixed solution may be preheated to adjust the time between the injection and the curing. The preheating may be carried out either under an ambient atmosphere or under an inert atmosphere (e.g., under a nitrogen atmosphere). Further, in order to prevent decomposition of the base resin and the curing agent, the humidity is preferably not more than 30% RH relative humidity. The heating rate after injection is preferably 0.5° C./min to 20° C./min, and more preferably 1° C./min to 10° C./min. If the heating rate is too fast, cracks may occur due to abnormal heat generation. Conversely, if the heating rate is too slow, degradation and volatilization of the base resin or curing agent tend to make it difficult to obtain an adhesive part having satisfactory properties. Further, the curing temperature may be controlled by gradual temperature increase or stepwise temperature decrease.

As described above, adhesive parts having satisfactory properties can be easily formed by controlling the mixing ratio of the base resin and curing agent, types thereof, curing temperature, and heating temperature. Ultimately, it is possible to obtain membrane modules for gas separation which can be used without deterioration of the performance over time.

After the curing of the adhesive, the membrane module for gas separation of the present embodiment can be obtained by cutting the ends of the fiber or fiber bundle in the adhesive part. The membrane module for gas separation of the present embodiment is provided with a housing, and optionally a header part, a footer part, etc., for practical use.

<Continuous Gas Supply System>

Figure 4:
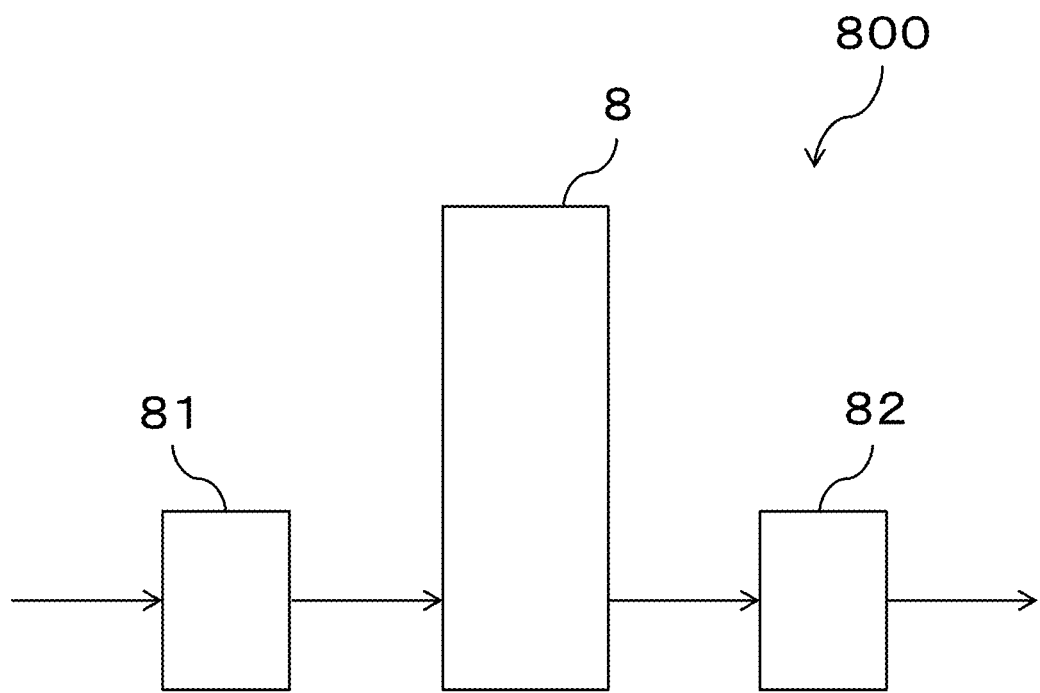
FIG. 4 is a schematic drawing showing an example of the configuration of the continuous gas supply system of the present embodiment.

Refer to FIG. 4. The present embodiment provides a continuous gas supply system 800 comprising at least a raw material gas inlet 81, a raw-gas purification part 8 for purifying a raw material gas to form a purified gas, and a purified gas outlet 82. The raw-gas purification part 8 comprises at least one selected from the group consisting of a membrane module for gas separation, a module loaded with an adsorbent, and a module loaded with an absorbent.

The raw material gas introduced into the continuous gas supply system from the raw material gas inlet 81 is purified to a desired purity (preferably 99.5% by mass or more) in the raw-gas purification part 8. The purified gas is directly supplied via the purified gas outlet 82 to sites where the high purity gas is used. In other words, the purified gas outlet 82 also serves as a high purity gas supply port. The gas supply port of the housing may be used as a raw material gas inlet, and the separation gas outlet of the housing may be used as a purified gas outlet.

[Raw-Gas Purification Part]

The raw-gas purification part 8 of the present embodiment comprises at least one of a membrane module for gas separation, a module loaded with an adsorbent, and a module loaded with an absorbent. In the present embodiment, a module of any mechanism may be used as long as the raw material gas can be purified while flowing, being taken out, and being supplied as a purified gas. However, a membrane module for gas separation is preferable because the occupied space can be reduced. As this membrane module for gas separation, those disclosed herein can be suitably used. A membrane module unit may be used in place of the membrane module for gas separation.

{Module Loaded with an Adsorbent}

The module loaded with an adsorbent of the present embodiment has at least an adsorption tank.

(Adsorption Tank)

The adsorption tank of the present embodiment has at least a gas introduction pipe and a gas delivery pipe and allows an adsorbent to adsorb a gas for the purpose of separation. The adsorption tank receives the adsorbent therein. The introduced gas is repeatedly subjected to the steps of adsorption, pressure equalization, desorption, washing, and pressurization, and is purified to the desired purity. The gas introduction pipe is open in the adsorption tank, and introduces the pressurized raw material gas into the tank. The gas delivery pipe delivers the purified gas to the outside the tank.

Examples of the adsorbent include alumina, silica, zeolite, and a porous MOF (Metal Organic Framework) comprising a mixture of a metal ion and an organic ligand.

{Module Loaded with an Absorbent}

The module loaded with an absorbent of the present embodiment has an absorption tower and a blowing-out tower.

(Absorption Tower)

The absorption tower of the present embodiment has at least a tower body, a gas introduction pipe, absorption liquid delivery pipe, and a gas delivery pipe, and contacts the raw material gas with an absorbent (typically, an absorption liquid) to carry out absorption. The tower body is a sealed container, and receives an absorbent (typically, an absorption liquid) therein.

When the gas for the purpose of separation is an olefin, examples of the absorbent include solutions, such as aqueous metal salt solutions and polyethylene glycol, aqueous solutions of cuprous chloride, and ionic liquids of imidazolium-based compounds and pyridinium-based compounds. Thereamong, metal salts are preferable.

The metal salt is preferably a metal salt containing a metal ion selected from the group consisting of monovalent silver ($Ag^+$) and monovalent copper ($Cu^+$) or a complex ion thereof, more preferably a metal salt composed of $Ag^+$, $Cu^+$, or a complex ion thereof and an anion selected from the group consisting of $F^-$, $Cl^-$, $Br^-$, $I^-$, $CN^-$, $NO_3^-$, $SCN^-$, $ClO_4^-$, $CF_3SO_3^-$, $BF_4^-$, and $PF_6^-$. Thereamong, $Ag(NO_3)$ is particularly preferable from the viewpoint of availability and product cost.

When the gas for the purpose of separation is carbon dioxide, examples of the absorbent include compounds having a nitrogen atom in the molecule (e.g., monoethanolamine), solutions thereof, and ionic liquids of imidazolium compounds and pyridinium compounds.

The gas introduction pipe has an open end which is open at the lower part of the absorbent inside the tower body, and introduces the raw material gas into the absorption tower. An absorbent delivery part has an end which is open in the absorbent within the tower body, and delivers the absorbent in the absorption tower to the outside the tower. Gas which has not been absorbed is delivered to the outside of the tower through the gas delivery pipe at the air layer part in the tower body.

(Blowing-Out Tower)

The blowing-out tower of the present embodiment has at least a tower body, an absorption liquid introduction pipe, a gas delivery pipe, and an absorption liquid delivery pipe, and blows out a gas absorbed in the absorption liquid. The blowing-out tower is equipped with a temperature maintaining device to maintain the absorption liquid at the desired temperature.

The absorption liquid introduction pipe has an end which is open at the lower part of the blowing-out tower, and introduces the absorption liquid delivered from the absorption tower into the blowing-out tower. The gas delivery pipe has an end which is open at the air layer part in the tower body, and delivers the purified gas blown out from the absorption liquid to the outside the tower. The absorption liquid delivery pipe has an end which is open at the lower part of the blowing-out tower, and delivers absorption liquid, from which the purified gas is blown out, to the outside the tower.

Preferred Example of the Continuous Gas Supply System

A preferred example of the continuous gas supply system of the present embodiment comprises a raw material gas inlet, a raw-gas purification part for purifying a raw material gas to form a purified gas, and a purified gas outlet. The purified gas has a purity of 99.5% by mass or more. The raw-gas purification part is a membrane module for gas separation, and is composed of a continuous gas supply system. The membrane module for gas separation satisfies the following a) and/or b):

a) in the gas separation membrane having a porous membrane and a gas separation active layer disposed on the porous membrane,
an interface between the porous membrane and the gas separation active layer does not have a dense layer or has a dense layer which is approximately parallel to the interface and has a thickness of less than 1 μm and an average pore diameter of less than 0.01 m,
A is 0.05 μm to 0.5 μm, and a ratio A/B is more than 0 to 0.9, wherein A is an average pore diameter in a depth range of the porous membrane ranging from the gas separation active layer to the depth of 2 μm and B is an average pore diameter in a depth range to the depth of 10 μm; and b) the adhesive part of the membrane module for gas separation satisfies at least one of the following (1) to (6):
1) the adhesive part has a low-mobility component having a composition ratio V (%), as measured by pulse NMR, wherein $30 \leq V \leq 100$;
2) the adhesive part has an attenuation rate W (%) represented by the following formula:

$$W=[(I1-I2)/I1]\times 100$$

wherein I1 is a signal intensity at start of measurement in the pulse NMR of the adhesive part, I2 is a signal intensity 0.05 msec after the measurement starts, and
wherein $30 \leq W \leq 100$;
3) the adhesive part has a change ratio X (%) represented by the following formula:

$$X=[(V2-V1)/V1]\times 100$$

wherein V1 and V2 respectively represent the composition rates V(V1(%)) and V(V2(%)) before and after immersion of the adhesive part in a 7 mol/L aqueous silver nitrate solution or heptane for 1 month at 25° C., and
wherein $-50 \leq X \leq 50$;
4) the adhesive part has a change ratio Y (%) represented by the following formula:

$$Y=[(W2-W1)/W1]\times 100$$

wherein W1 and W2 respectively represent the attenuation rates W(W1(%)) and W(W2(%)) before and after immersion of the adhesive part in a 7 mol/L aqueous silver nitrate solution or heptane for 1 month at 25° C., respectively, and
wherein $-120 \leq Y \leq 120$;
5) the adhesive part has a nitrogen atom content ($C_N$, % by mass), wherein $0.0010 \leq C_N \leq 10$, and a sulfur atom content ($C_S$, % by mass), wherein $0.0010 \leq C_S \leq 0.01$; and
6) the adhesive part has a hardness K, wherein $10D \leq K \leq 90D$; and the membrane module for gas separation comprises the following mechanisms c) and d):

c) a humidifying mechanism for humidifying a raw material gas to be supplied to the gas separation membrane; and
d) a dehydration mechanism disposed downstream of the membrane module.

<Membrane Module Unit>

Figure 5:
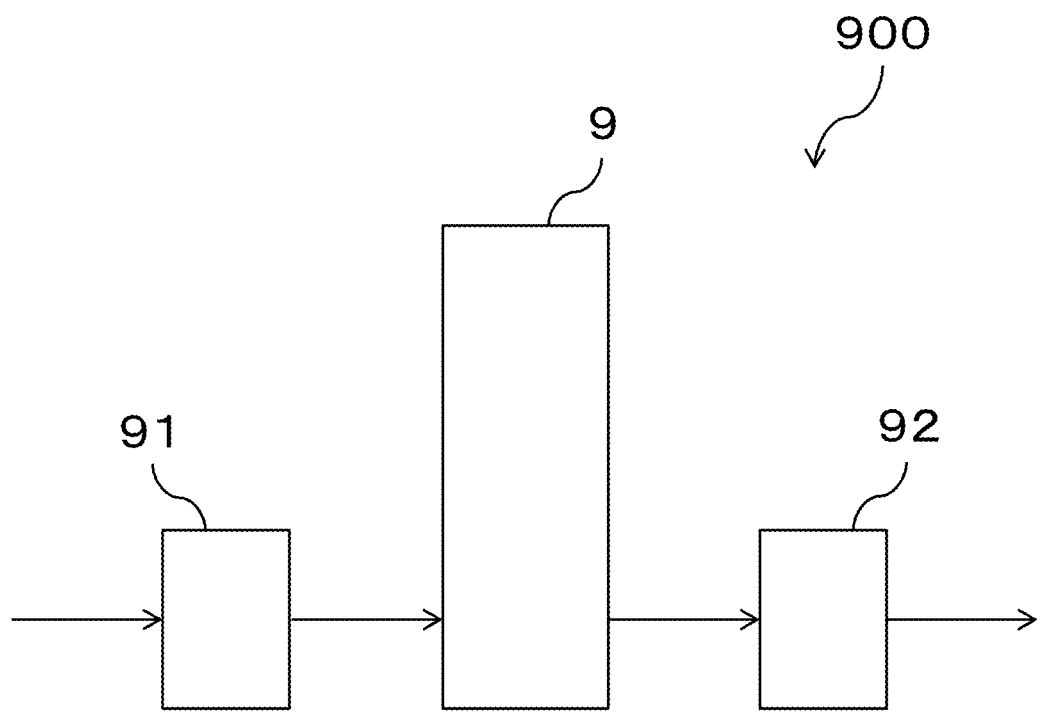
FIG. 5 is a schematic drawing showing an example of the configuration of the membrane module unit of the present embodiment.

Refer to FIG. 5. The present embodiment provides a membrane module unit comprising the membrane module for gas separation disclosed herein. The membrane module unit of the present embodiment 900 can effectively remove inorganic impurities and organic impurities for a long period of time as a membrane module unit which comprises the following mechanisms a), b), and c) and satisfies at least one of d) and e).

a) a membrane module for gas separation 9, comprising: a housing; a gas separation membrane disposed in the housing; and an adhesive part for affixing the gas separation membrane to the housing, b) a humidifying mechanism 91 for humidifying a raw material gas to be supplied to the gas separation membrane; and c) a dehydration mechanism 92 for dehydrating a gas purified by the gas separation membrane;

d) the gas separation membrane for forming a membrane module for gas separation is a gas separation membrane having a gas separation active layer on the porous membrane, an interface between the porous membrane and the gas separation active layer does not have a dense layer or has a dense layer which is approximately parallel to the interface and has a thickness of less than 1 μm and an average pore diameter of less than 0.01 m, A is 0.05 μm to 0.5 μm, and a ratio A/B is more than 0 to 0.9, wherein A is an average pore diameter in a depth range of the porous membrane ranging from the gas separation active layer to the depth of 2 μm and B is an average pore diameter in a depth range to the depth of 10 μm;

e) the adhesive part of the membrane module for gas separation satisfies at least one of the following (1) to (6):

1) the adhesive part has a low-mobility component having a composition ratio V (%), as measured by pulse NMR, wherein $30 \leq V \leq 100$;

2) the adhesive part has an attenuation rate W (%) represented by the following formula:

$$W=[(I1-I2)/I1] \times 100$$

wherein I1 is a signal intensity at the start of measurement in the pulse NMR of the adhesive part, I2 is a signal intensity 0.05 msec after the measurement starts, and wherein $30 \leq W \leq 100$;

3) the adhesive part has a change ratio X (%) represented by the following formula:

$$X=[(V2-V1)/V1] \times 100$$

wherein V1 and V2 respectively represent the composition rates V(V1(%)) and V(V2(%)) before and after immersion of the adhesive part in a 7 mol/L aqueous silver nitrate solution or heptane for 1 month at 25° C., and wherein $-50 \leq X \leq 50$;

4) the adhesive part has a change ratio Y (%) represented by the following formula:

$$Y=[(W2-W1)W1] \times 100$$

wherein W1 and W2 respectively represent the attenuation rates W(W1(%)) and W(W2(%)) before and after immersion of the adhesive part in a 7 mol/L aqueous silver nitrate solution or heptane for 1 month at 25° C., respectively, and wherein $-120 \leq Y \leq 120$;

5) the adhesive part has a nitrogen atom content ($C_N$, % by mass), wherein $0.0010 \leq C_N \leq 10$, and a sulfur atom content ($C_S$, % by mass), wherein $0.0010 \leq C_S \leq 0.01$; and 6) the adhesive part has a hardness K, wherein $10D \leq K \leq 90D$.

[Humidifying Mechanism]

The membrane module unit of the present embodiment comprises a humidifying mechanism. The humidifying mechanism is preferably disposed upstream of the membrane module for gas separation or in the membrane module for gas separation. The humidifying mechanism disposed upstream of the membrane module for gas separation may be, for example, a bubbler. Due to the bubbling of the raw material gas in water, the gas is accompanied by moisture at a temperature in accordance with the bubbler temperature. The humidifying mechanism disposed in the membrane module for gas separation may be, for example, a mechanism of an aqueous solution loaded in the gas separation membrane on the gas separation active layer side or a mechanism of a spray nozzle disposed in the housing to supply mist shower. With the humidifying mechanism, inorganic impurities in the raw material gas can be dissolved in water.

[Dehydration Mechanism]

The membrane module unit of the present embodiment comprises a dehydration mechanism downstream of the membrane module for gas separation. The dehydration mechanism may be, for example, a mist separator or an adsorbent, such as alumina or zeolite. With the dehydration mechanism, inorganic impurities dissolved in water can be removed together with water.

[Gas Purity Detection System]

The membrane module unit of the present embodiment preferably comprises a gas purity detection system capable of measuring purified gas purity on-line in the system. Examples of the gas purity detection system include a gas chromatography mass spectrometer, a gas chromatograph hydrogen flame ionization detector, a gas chromatograph thermal conductivity detector, a gas chromatographic frame photometric detector, and ion chromatography.

Preferred Example of the Membrane Module Unit

A preferred example of the membrane module unit of the present embodiment is a membrane module unit for forming a gas purification system which comprises a membrane module for gas separation, a humidifying mechanism, and a dehydration mechanism, and which is of a gas flow type, and in which the purity of a purified gas is 99.5% by mass or more, and in which the membrane module for gas separation satisfies the following requirements a) and/or b): a) in the gas separation membrane having a porous membrane and a gas separation active layer disposed on the porous membrane, an interface between the porous membrane and the gas separation active layer does not have a dense layer or has a dense layer which is approximately parallel to the interface and has a thickness of less than 1 μm and an average pore diameter of less than 0.01 μm, A is 0.05 μm to 0.5 μm, and a ratio A/B is more than 0 to 0.9, wherein A is an average pore diameter in a depth range of the porous membrane ranging from the gas separation active layer to the depth of 2 μm and B is an average pore diameter in a depth range to the depth of 10 μm;

b) the adhesive part of the membrane module for gas separation satisfies at least one of the following (1) to (6):

1) the adhesive part has a low-mobility component having a composition ratio V (%), as measured by pulse NMR, wherein $30 \leq V \leq 100$;

2) the adhesive part has an attenuation rate W (%) represented by the following formula:

$$W=[(I1-I2)/I1]\times 100$$

wherein I1 is a signal intensity at the start of measurement in the pulse NMR of the adhesive part, I2 is a signal intensity 0.05 msec after the measurement starts, and
wherein $30 \leq W \leq 100$;
3) the adhesive part has a change ratio X (%) represented by the following formula:

$$X=[(V2-V1)/V1]\times 100$$

wherein V1 and V2 respectively represent the composition rates V(V1(%)) and V(V2(%)) before and after immersion of the adhesive part in a 7 mol/L aqueous silver nitrate solution or heptane for 1 month at 25° C., and
wherein $-50 \leq X \leq 50$;
4) the adhesive part has a change ratio Y (%) represented by the following formula:

$$Y=[(W2-W1)/W1]\times 100$$

wherein W1 and W2 respectively represent the attenuation rates W(W1(%)) and W(W2(%)) before and after immersion of the adhesive part in a 7 mol/L aqueous silver nitrate solution or heptane for 1 month at 25° C., respectively, and
wherein $-120 \leq Y \leq 120$;
5) the adhesive part has a nitrogen atom content ($C_N$, % by mass), wherein $0.0010 \leq C_N \leq 10$, and a sulfur atom content ($C_S$, % by mass), wherein $0.0010 \leq C_S \leq 0.01$; and
6) the adhesive part has a hardness K, wherein $10D \leq K \leq 90D$.

In a particularly preferred aspect, the membrane module unit is configured to provide, as a purified gas, an olefin gas having a purity of 99.9% by mass or more.

The membrane module unit of a preferred aspect has a gas separation active layer composed of a polymer having one or more functional groups selected from the group consisting of an amino group, a pyridyl group, an imidazolyl group, an indolyl group, a hydroxyl group, a phenol group, an ether group, a carboxyl group, an ester group, an amide group, a carbonyl group, a thiol group, a thioether group, a sulfone group, a sulfonyl group, and a sulfonamide group. In a more preferred aspect, the gas separation active layer is composed of a polymer having one or more functional groups selected from the group consisting of an amino group, a sulfone group, and a hydroxyl group. In a further preferred aspect, the polymer is a polyamine. In an even further preferred aspect, the polyamine is a chitosan.

The membrane module unit of a preferred aspect has a gas separation membrane containing monovalent Ag and/or monovalent Cu.

The membrane module unit of a preferred aspect has a porous membrane containing a fluororesin. The fluororesin is preferably PVDF.

In the continuous gas supply system or the membrane module unit of a preferred aspect, a separation factor of propylene/propane is preferably 50 to 100,000, as measured using a mixed gas composed of 40% by mass of propane and 60% by mass of propylene with respect to the membrane module for gas separation at a supply side gas flow rate of 190 cc/min per 2 cm$^2$ membrane area and a permeation side gas flow rate of 50 cc/min per 2 cm$^2$ membrane area in a humidified atmosphere under isobaric conditions at 30° C.

The present embodiment provides a method for producing an olefin gas having a purity of 99.5% by mass or more by the use of the above continuous gas supply system or membrane module unit. The olefin gas may be, for example, propylene for CVD supply.

EXAMPLES

The present invention will be explained below in more detail, referring to the Examples, etc. However, the present invention is not limited to these Examples, etc.

<Adhesive>

In the following Examples and Comparative Example, the two-part epoxy resin adhesive and polyurethane resin adhesive shown in Table 1 were used. A base resin and a curing agent were mixed at the mixing ratio shown in Table 1, cured under the conditions shown in Table 1, and were used as an adhesive part.

TABLE 1

| Adhesive name | Base resin | | Curing agent | | Curing conditions |
| | structure | mixing ratio (mass %) | structure | mixing ratio (mass %) | |
|---|---|---|---|---|---|
| A | alicyclic epoxy | 50 | alicyclic acid anhydride | 50 | 110° C., 3 h → 130° C., 3 h |
| B | alicyclic epoxy | 65 | alicyclic acid anhydride | 35 | 110° C., 3 h → 130° C., 3 h |
| C | alicyclic epoxy | 45 | alicyclic acid anhydride | 55 | 110° C., 3 h → 130° C., 3 h |
| D | Bis-A epoxy | 40 | alicyclic acid anhydride | 60 | 120° C., 3 h |
| E | naphthalene epoxy | 75 | alicyclic acid anhydride | 25 | 120° C., 90 min |
| F | alicyclic epoxy | 75 | alicyclic acid anhydride | 25 | 110° C., 3 h → 130° C., 3 h |
| G | Bis-A epoxy | 75 | polyamide/polyamine mixture (40:60 (mass ratio)) | 25 | 25° C., 12 h → 70° C., 1 h → 120° C., 2 h |
| H | Bis-A epoxy + aliphatic epoxy | 80 | polyamide/polyamine mixture (40:60 (mass ratio)) | 20 | 25° C., 12 h → 70° C., 1 h → 120° C., 2 h |
| I | Bis-A epoxy | 75 | alicyclic amine | 25 | 70° C., 2 h → 150° C., 2 h |
| J | castor oil-based polyol | 50 | hexamethylene diisocyanate | 50 | 60° C., 12 h |
| K | castor oil-based polyol | 60 | hexamethylene diisocyanate | 40 | 60° C., 12 h |
| L | castor oil-based polyol | 30 | hexamethylene diisocyanate | 70 | 60° C., 12 h |
| M | polyacrylic polyol | 50 | 4,4'-diphenylmethane diisocyanate | 50 | 40° C., 12 h → 100° C., 6 h |
| N | castor oil-based polyol | 20 | hexamethylene diisocyanate | 80 | 60° C., 12 h |

<Pulse NMR Measurement of an Adhesive Cured Product>

Analysis Examples 1-1 to 1-14

A plate-like body was formed from a cured product of an adhesive using each of adhesives A to N at the mixing ratio of a base resin and a curing agent under the curing conditions shown in Table 1.

Adhesives A, B, C, and F were product name HV/ME-562 available from Belnox. D was product name HV/ME-541 available from Belnox. E was EPH-01X available from Muromachi Chemicals. Adhesives G and H were product names 193316/193317 available from Henkel. Adhesive I was product name E-90FL available from Henkel. Adhesives J, K, L, and N were product names SA-7702A/7702B2 available from Sunyu Rec. Adhesive M was product name SA-6333A2/B5 available from Sunyu Rec.

The plate-like body was cut into an adhesive test piece having a length of 70 mm, a width of 5 mm, and a thickness of 1 mm for an immersion test.

The conditions for carrying out each test were as follows.

Non-immersed product: A non-immersed product was left standing in a constant temperature and humidity room at 25° C. and a relative humidity of 40% RH for 24 h to adjust the state, and was subjected to pulse NMR measurement.

After immersion in an aqueous silver nitrate solution: A test piece was immersed in 7 mol/L aqueous silver nitrate solution (silver nitrate according to JIS K 8550J was used) at a liquid temperature of 25° C. for 1 month. The aqueous silver nitrate solution was wiped off and the test piece was washed with distilled. Thereafter, the test piece was subjected to pulse NMR measurement.

After immersion in heptane: A test piece was immersed in heptane at a liquid temperature of 25° C. for 1 month. The heptane was wiped off and the test piece was subjected to pulse NMR measurement.

The conditions for carrying out pulse NMR were as follows. First, a measurement sample cut into a height of 1.5 cm was put into a glass tube having an outer diameter 10 mm. Minispec MQ20 available from Bruker Biosipn, Inc., was used. The glass tube containing the test piece was placed in the device controlled at a temperature of 190° C. After 5 minutes had lapsed, the relaxation time T2 of 1H was measured by a solid echo method. For the measurement, the repeated standby time during the measurement was set to be not less than 5 times larger than the relaxation time T1 of the sample. Fitting of the thus-obtained magnetization decay curve was carried out using formula I consisting a Weibull function and a Lorenz function. The low-mobility component was a component represented using a Weibull function. The high-mobility component was a component represented using a Lorenz function. The software used for the fitting was Igor Pro6. The fitting was performed using the initial value of Weibull coefficient of 2.0 such that the Weibull coefficient was 1.2 to 2.0. The fitting was performed using relaxation time Ts of the low-mobility component of 0.02 msec and relaxation time T1 of the high-mobility component of 0.1 msec. The fitting range was from 0 msec to 0.4 msec.

According to the above procedures, from the magnetization decay curve obtained using pulse NMR, an initial signal intensity (I1) at the start of measurement at the time of acquisition start and a signal intensity (I2) at 0.05 msec were obtained. The attenuation rate (W, %) of signal intensity at 0.05 msec was calculated using I1, I2, and mathematical formula 2

[Math. 2]

$$\text{Attenuation rate } (W, \%) \text{ of signal intensity at 0.05 msec} = [(I1-I2)/I1] \times 100 \quad (2)$$

The analysis results of each adhesive by pulse NMR are shown in Table 2.

TABLE 2

| | Adhesive type | Before immersion | | After immersion in 7 mol/L aqueous silver nitrate solution | | After immersion in heptane | |
|---|---|---|---|---|---|---|---|
| | | low-mobility component composition ratio V (%) | signal intensity attenuation rate W (%) | low-mobility component composition ratio V change ratio X (%) | signal intensity attenuation rate W change ratio Y (%) | low-mobility component composition ratio V change ratio X (%) | signal intensity attenuation rate W change ratio Y (%) |
| Analysis Example 1-1 | A | 96 | 98 | 1.6 | 0.72 | 0.52 | 1.3 |
| Analysis Example 1-2 | B | 38 | 33 | — | — | — | — |
| Analysis Example 1-3 | C | 94 | 96 | — | — | — | — |
| Analysis Example 1-4 | D | 79 | 67 | — | — | — | — |
| Analysis Example 1-5 | E | 54 | 34 | 42 | 104 | 16 | 50 |
| Analysis Example 1-6 | F | 28 | 27 | — | — | — | — |
| Analysis Example 1-7 | G | 29 | 27 | — | — | — | — |
| Analysis Example 1-8 | H | 26 | 23 | — | — | — | — |
| Analysis Example 1-9 | I | 21 | 28 | — | — | — | — |

TABLE 2-continued

|  | Adhesive type | Before immersion | | After immersion in 7 mol/L aqueous silver nitrate solution | | After immersion in heptane | |
|---|---|---|---|---|---|---|---|
|  |  | low-mobility component composition ratio V (%) | signal intensity attenuation rate W (%) | low-mobility component composition ratio V change ratio X (%) | signal intensity attenuation rate W change ratio Y (%) | low-mobility component composition ratio V change ratio X (%) | signal intensity attenuation rate W change ratio Y (%) |
| Analysis Example 1-10 | J | 93 | 94 | — | — | — | — |
| Analysis Example 1-11 | K | 92 | 83 | — | — | — | — |
| Analysis Example 1-12 | L | 75 | 65 | — | — | — | — |
| Analysis Example 1-13 | M | 37 | 42 | — | — | — | — |
| Analysis Example 1-14 | N | 29 | 25 | — | — | — | — |

<Measurement of the N Content and S Content of an Adhesive Cured Product>

Analysis Examples 2-1 to 2-14

A plate-like body was formed from a cured product of an adhesive using each of adhesives A to N at the mixing ratio of a base resin and a curing agent under the curing conditions shown in Table 1. The plate-like body was dried at 50° C. under reduced pressure for 24 h. Thereafter, the nitrogen (N) content $C_N$ (% by mass) was analyzed by a CHN coder (carbon, hydrogen, and nitrogen simultaneous determination device), and the sulfur (S) content $C_S$ (% by mass) was analyzed by an ion chromatography method.

The obtained results are shown in Table 3 together with the ratio $C_N/C_S$ of both of the contents.

The expression "<0.30" in the N content column in Table 2 indicates that the N content was below the N content detection limit (0.30% by mass) of the CHN coder.

TABLE 3

|  | Adhesive type | Content (mass %) | | $C_N/C_S$ ratio |
|---|---|---|---|---|
|  |  | N content $C_N$ | S content $C_S$ |  |
| Analysis Example 2-1 | A | <0.30 | 0.0050 | <60.0 |
| Analysis Example 2-2 | B | <0.30 | 0.0050 | <60.0 |
| Analysis Example 2-3 | C | <0.30 | 0.0050 | <60.0 |
| Analysis Example 2-4 | D | <0.30 | 0.0070 | <42.9 |
| Analysis Example 2-5 | E | <0.30 | 0.0070 | <42.9 |
| Analysis Example 2-6 | F | <0.30 | 0.0050 | <60.0 |
| Analysis Example 2-7 | G | 4.0 | 0.010 | 400 |
| Analysis Example 2-8 | H | 9.5 | 0.0070 | 1357 |
| Analysis Example 2-9 | I | 12 | 0.0008 | 15000 |
| Analysis Example 2-10 | J | 3.9 | 0.0060 | 650 |
| Analysis Example 2-11 | K | 3.8 | 0.0050 | 760 |
| Analysis Example 2-12 | L | 3.8 | 0.0050 | 760 |
| Analysis Example 2-13 | M | 9.7 | 0.0090 | 10778 |
| Analysis Example 2-14 | N | 14 | 0.0090 | 15556 |

<Measurement of the Hardness of an Adhesive Cured Product>

Analysis Examples 3-1 to 3-14

A plate-like body was formed from a cured product of an adhesive using each of adhesives A to N at the mixing ratio of a base resin and a curing agent under the curing conditions shown in Table 1.

The plate-like body was dried at 50° C. under reduced pressure for 24 h, and thereafter, was analyzed by a method according to JISK6253 and ISO7619.

The obtained results are shown in Table 4.

TABLE 4

|  | Adhesive type | Hardness K |
|---|---|---|
| Analysis Example 3-1 | A | 87 |
| Analysis Example 3-2 | B | 32 |
| Analysis Example 3-3 | C | 75 |
| Analysis Example 3-4 | D | 47 |
| Analysis Example 3-5 | E | 31 |
| Analysis Example 3-6 | F | 20 |
| Analysis Example 3-7 | G | 21 |
| Analysis Example 3-8 | H | 24 |
| Analysis Example 3-9 | I | 9 |
| Analysis Example 3-10 | J | 89 |
| Analysis Example 3-11 | K | 74 |
| Analysis Example 3-12 | L | 62 |
| Analysis Example 3-13 | M | 34 |
| Analysis Example 3-14 | N | 8 |

<Chemical Resistance Test of an Adhesive Cured Product>

Test Examples 1 to 3

A plate-like body was formed from a cured product of an adhesive using each of adhesives A (Test Example 1), D (Test Example 2), E (Test Example 3), and J (Test Example 4) at the mixing ratio of a base resin and a curing agent under the curing conditions shown in Table 1. The plate-like body was cut into an adhesive test piece having a length of 70 mm, a width of 5 mm, and a thickness of 1 mm for an immersion test.

As many test pieces as necessary for the measurements of the bending Young's modulus and bending strength for the 3 cases were prepared: after immersion in heptane; after immersion in an aqueous silver nitrate solution; and a non-immersed product at the following repetition number N. The mass and the thickness were measured. The number of samples was the following number N, and each sample was measured twice, i.e., before and after immersion.

The conditions for carrying out each test were as follows.

A non-immersed product was left standing in a constant temperature and humidity room at 25° C. and a relative humidity of 40% RH for 24 h to adjust the state, and was subjected to each analysis.

After immersion in an aqueous silver nitrate solution: A test piece was immersed in 7 mol/L aqueous silver nitrate solution (silver nitrate according to JIS K 8550J was used) at a liquid temperature of 25° C. for 1 month. The aqueous silver nitrate solution was wiped off and the test piece was washed with distilled. Thereafter, the test piece was subjected to each analysis.

After immersion in heptane: A test piece was immersed in heptane at a liquid temperature of 25° C. for 1 month. The heptane was wiped off and the test piece was subjected to each analysis.

Bending Young's modulus and bending strength: measured by a three point bending test method using Type "TG-1KN" available from Minebea at a test temperature of 25° C., a test speed of 5 mm/sec and with a number of N=5. Mass: measured using an analytical electronic balance with N number=5.

Thickness: The thickness of one sample was the average of values measured at five measurement points selected at random.

The results of chemical resistance test of each adhesive are shown in Table 5.

the adhesive was completely cured, 1 cm of each cylinder end was cut. Further, a footer part 3 having a gas supply port 31 and a header part 4 having process gas outlet 41 was installed in the container 2 to produce a membrane module for gas separation 100.

The permeation rates of propane and propylene were measured using the above membrane module for gas separation 100.

The measurement was carried out by supplying a mixed gas composed of propane and propylene (propane:propylene=40:60 (mass ratio)) to a gas supply port 31 and supplying helium to a permeable fluid inlet 21 at a supply gas flow rate of 190 cc/min and a permeation gas flow rate of 50 cc/min in a humidified atmosphere under isobaric conditions at 30° C.

The results on day 1 were calculated from the composition of the gas which permeated the membrane module for gas separation 100 and was discharged from a separation gas outlet 22, 3 hours after the start of supply of the mixed gas consisting of propane and propylene. The results on day 7 were obtained 7 days after the start of the supply. The separation gas was analyzed by gas chromatography (GC).

TABLE 5

| Adhesive type | After immersion in 7 mol/L aqueous silver nitrate solution | | | | After immersion in heptane | | | |
| --- | --- | --- | --- | --- | --- | --- | --- | --- |
| | Test Example 1 A | Test Example 2 D | Test Example 3 E | Test Example 4 J | Test Example 1 A | Test Example 2 D | Test Example 3 E | Test Example 4 J |
| Young's modulus change (%) | −2.58 | −12.81 | −16.58 | +1.39 | +25.8 | +7.95 | +23.6 | +12.4 |
| Strength change (%) | −1.66 | −17.08 | +37.4 | −1.87 | +0.95 | −7.61 | +64.1 | +2.32 |
| Mass change (mg/cm$^2$) | +1.43 | +1.65 | +3.14 | +2.87 | −1.56 | −1.96 | −5.43 | −3.24 |
| Thickness change (%) | −0.982 | +1.14 | +2.81 | +3.98 | +0.764 | +1.54 | +3.02 | +3.56 |

<Performance Test of a Membrane Module for Gas Separation>

Examples 1-1 to 1-20 and Comparative Examples 1-1 and 1-2

A membrane module for gas separation as shown FIG. 1 was formed.

10 gas separation membranes composed of hollow fiber membranes consisting of the resin shown in Table 1 and having an inner diameter of 0.7 mm, an outer diameter of 1.2 mm, and a length of 7.1 cm, or the hollow fiber membranes having the gas separation active layers shown in Table 1 disposed in the inner surface thereof were used; and the housing used was composed of a combination of a cylindrical container 2 (inner diameter 2 cm) having a permeable gas inlet 21 and a separation gas outlet 22 with a footer part 3 having a gas supply port 31 and a header part 4 having a process gas outlet 41.

10 gas separation membranes 6 were put into the cylindrical container 2. The adhesive shown in Table 1 was used and cured under the conditions shown in Table 1 to obtain an adhesive part 10, whereby the gas separation membrane was adhesively sealed at both ends of the container 2. After The analysis results are shown in Tables 7 and 8.

The coating solutions shown in Table 6 were used and Examples 1-2 to 1-20 and Comparative Example 1-1 and 1-2 were analyzed under the conditions shown in Table 7 in the same manner as Examples 1-1.

The results are shown in Tables 7 and 8.

TABLE 6

| | Gas separation active layer material | | | | |
| --- | --- | --- | --- | --- | --- |
| | | number average | | Other components | |
| | type | molecular weight | concentration | type | concentration |
| a | chitosan | 500,000 | 1 mass % | glycerin | 1 mass % |
| | | | | acetic acid | 1 mass % |
| b | chitosan | 500,000 | 0.5 mass % | FC-4430 | 0.01 mass % |
| | | | | acetic acid | 0.5 mass % |
| c | Nafion | — | 5 mass % | — | — |
| d | chitosan | 500,000 | 4 mass % | acetic acid | 2 mass % |

TABLE 7

| | Gas separation membrane | | | | | Pulse NMR analysis value | |
|---|---|---|---|---|---|---|---|
| | porous membrane type | shape | membrane area (cm²) | gas separation active layer | coating solution when coating | Adhesive type | low-mobility component composition ratio V (%) | signal intensity attenuation rate W (%) |
| Example 1-1 | PVDF | hollow fiber membrane | 27 | — | a | A | 96 | 98 |
| Example 1-2 | PVDF | hollow fiber membrane | 27 | chitosan | a | A | 96 | 98 |
| Example 1-3 | PSU | hollow fiber membrane | 27 | chitosan | a | A | 96 | 98 |
| Example 1-4 | PVDF | hollow fiber membrane | 27 | chitosan | a | B | 38 | 33 |
| Example 1-5 | PVDF | hollow fiber membrane | 27 | chitosan | a | C | 94 | 96 |
| Example 1-6 | PVDF | hollow fiber membrane | 27 | chitosan | a | D | 79 | 67 |
| Example 1-7 | PVDF | hollow fiber membrane | 27 | chitosan | a | E | 54 | 34 |
| Example 1-8 | PES | flat sheet membrane | 27 | — | — | A | 96 | 98 |
| Example 1-9 | PES | flat sheet membrane | 27 | chitosan | a | A | 96 | 98 |
| Example 1-10 | PVDF | hollow fiber membrane | 27 | chitosan | a | G | 29 | 27 |
| Example 1-11 | PVDF | hollow fiber membrane | 27 | chitosan | a | H | 26 | 23 |
| Example 1-12 | PVDF | hollow fiber membrane | 27 | chitosan | a | F | 28 | 27 |

| | Elemental analysis value | | | Hardness | Evaluation results | | |
|---|---|---|---|---|---|---|---|
| | N content $C_N$ | S content $C_S$ | $C_N/C_S$ ratio | analysis value hardness K | measurement date | propylene permeation rate (GPU) | propylene/propane separation factor |
| Example 1-1 | <0.30 | 0.0050 | <60.0 | 87 | Day 1 | 103 | >300 |
| | | | | | Day 7 | 83 | >300 |
| Example 1-2 | <0.30 | 0.0050 | <60.0 | 87 | Day 1 | 154 | >300 |
| | | | | | Day 7 | 146 | >300 |
| Example 1-3 | <0.30 | 0.0050 | <60.0 | 87 | Day 1 | 154 | >300 |
| | | | | | Day 7 | 158 | >300 |
| Example 1-4 | <0.30 | 0.0050 | <60.0 | 32 | Day 1 | 153 | >300 |
| | | | | | Day 7 | 115 | 105 |
| Example 1-5 | <0.30 | 0.0050 | <60.0 | 75 | Day 1 | 201 | >300 |
| | | | | | Day 7 | 197 | >300 |
| Example 1-6 | <0.30 | 0.0070 | <42.9 | 47 | Day 1 | 164 | >300 |
| | | | | | Day 7 | 156 | 224 |
| Example 1-7 | <0.30 | 0.0070 | <42.9 | 31 | Day 1 | 168 | >300 |
| | | | | | Day 7 | 123 | 187 |
| Example 1-8 | <0.30 | 0.0050 | <60.0 | 87 | Day 1 | 120 | >300 |
| | | | | | Day 7 | 93 | >300 |
| Example 1-9 | <0.30 | 0.0050 | <60.0 | 87 | Day 1 | 143 | >300 |
| | | | | | Day 7 | 148 | >300 |
| Example 1-10 | 4.0 | 0.010 | 400 | 21 | Day 1 | 153 | 231 |
| | | | | | Day 7 | 72 | 109 |
| Example 1-11 | 9.5 | 0.0070 | 1357 | 24 | Day 1 | 156 | 213 |
| | | | | | Day 7 | 68 | 110 |
| Example 1-12 | <0.30 | 0.0050 | <60.0 | 20 | Day 1 | | |
| | | | | | Day 7 | | |
| | | | | | Day 7 | | |

TABLE 8

| | Gas separation membrane | | | | | Pulse NMR analysis value | |
|---|---|---|---|---|---|---|---|
| | porous membrane type | shape | membrane area (cm²) | gas separation active layer | coating solution when coating | Adhesive type | low-mobility component composition ratio V (%) | signal intensity attenuation rate W (%) |
| Example 1-13 | PVDF | hollow fiber membrane | 27 | chitosan | a | J | 93 | 94 |
| Example 1-14 | PVDF | flat sheet membrane | 27 | chitosan | a | J | 93 | 94 |

TABLE 8-continued

| | | | | | | | | |
|---|---|---|---|---|---|---|---|---|
| Example 1-15 | PVDF | hollow fiber membrane | 27 | Nafion | c | J | 93 | 94 |
| Example 1-16 | PVDF | hollow fiber membrane | 27 | — | — | J | 93 | 94 |
| Example 1-17 | PVDF | hollow fiber membrane | 27 | chitosan | a | K | 92 | 83 |
| Example 1-18 | PVDF | hollow fiber membrane | 27 | chitosan | a | K | 92 | 83 |
| Example 1-19 | PVDF | hollow fiber membrane | 27 | chitosan | a | L | 75 | 65 |
| Example 1-20 | PVDF | hollow fiber membrane | 27 | chitosan | a | M | 37 | 42 |
| Comp. Ex. 1-1 | PVDF | hollow fiber membrane | 27 | chitosan | a | I | 21 | 28 |
| Comp. Ex. 1-2 | PVDF | hollow fiber membrane | 27 | chitosan | a | N | 29 | 25 |

| | Elemental analysis value | | | Hardness | Evaluation results | | |
|---|---|---|---|---|---|---|---|
| | N content $C_N$ | S content $C_S$ | $C_N/C_S$ ratio | analysis value hardness K | measurement date | propylene permeation rate (GPU) | propylene/propane separation factor |
| Example 1-13 | 3.9 | 0.0060 | 650 | 89 | Day 1 Day 7 | | |
| Example 1-14 | 3.9 | 0.0060 | 650 | 89 | Day 1 Day 7 | | |
| Example 1-15 | 3.9 | 0.0060 | 650 | 89 | Day 1 Day 7 | | |
| Example 1-16 | 3.9 | 0.0060 | 650 | 89 | Day 1 Day 7 | | |
| Example 1-17 | 3.8 | 0.0050 | 760 | 74 | Day 1 Day 7 | | |
| Example 1-18 | 3.8 | 0.0050 | 760 | 74 | Day 1 Day 7 | | |
| Example 1-19 | 3.8 | 0.0050 | 760 | 62 | Day 1 Day 7 | | |
| Example 1-20 | 9.7 | 0.0090 | 10778 | 34 | Day 1 Day 7 | | |
| Comp. Ex. 1-1 | 12 | 0.0080 | 15000 | 9 | Day 1 Day 7 | 167 25 | 223 48 |
| Comp. Ex. 1-2 | 14 | 0.0090 | 15556 | 8 | Day 1 Day 7 | | |

In the table, the component abbreviations in the porous membrane type column have the following meanings (the same applies below).

PVDF: Polyvinylidene fluoride
PSU: polysulfone
PES: polyethersulfone

<Performance Test of a Membrane Module Unit>

A gas separation membranes was immersed in 0.8M sodium hydroxide solution (solvent=ethanol:water (80:20 by volume)) for 1 day, and was thereafter washed 5 times with distilled water. This gas separation membrane was cut to 15 cm. 10 pieces were formed into one bundle to form a gas separation membrane module using the adhesive shown in Table 3.

Thereafter, this gas separation membrane module was immersed in 7M aqueous silver nitrate solution for 24 h to obtain a gas separation membrane containing a silver salt. This gas separation membrane containing a silver salt was used to measure the permeation rates of propane and propylene.

Examples 2-1 to 2-6, 2-8, and 2-11 were measured using a gas purification system in which 99.5% by mass of propylene (containing propane, carbon monoxide, carbon dioxide, ammonia, oxygen, nitrogen, NOx, etc., as impurities) containing water vapor added in a bubble type manner at 28.5° C. was supplied at 190 cc/min and 30° C. to the membrane module for gas separation, and was dehydrated by an alumina adsorbent.

Examples 2-7 and 2-12 were measured using a gas purification system in which 99.5% by mass of propylene (containing propane, carbon monoxide, carbon dioxide, ammonia, oxygen, nitrogen, NOx, etc., as impurities) was supplied at 190 cc/min and 30° C. to a membrane module for gas separation loaded with 7 M aqueous silver nitrate solution, and was dehydrated by an alumina adsorbent. Example 2-13 was measured using a gas purification system in which 99.5% by mass of propylene (containing propane, carbon monoxide, carbon dioxide, ammonia, oxygen, nitrogen, NOx, etc., as impurities) was directly supplied at 190 cc/min and 30° C. to a membrane module for gas separation.

The results on day 1 were calculated from the composition of the gas which was discharged from the gas purification system, 3 hours after the start of supply of the raw material gas. The results on day 7 were obtained 7 days after the start of the supply.

Examples 2-1

A hollow fiber made of polyvinylidene fluoride was used as a porous membrane. The outer diameter, the inner diameter, and the average pore diameters A and B thereof are shown in Table 9.

The length of the hollow fiber support was 25 cm. Both ends were heat sealed. The hollow fiber support was immersed into a coating solution A (liquid temperature 25°

C.) having the following composition at a rate of 1 cm/sec. The whole of the support was submerged in the above aqueous solution and was left standing for 5 sec. Thereafter, the support was pulled out at a rate of 1 cm/sec, and was heated at 120° C. for 10 min to form a gas separation active layer on an outer surface of the hollow fiber support, whereby a hollow fiber gas separation membrane was produced.

Figure 7:
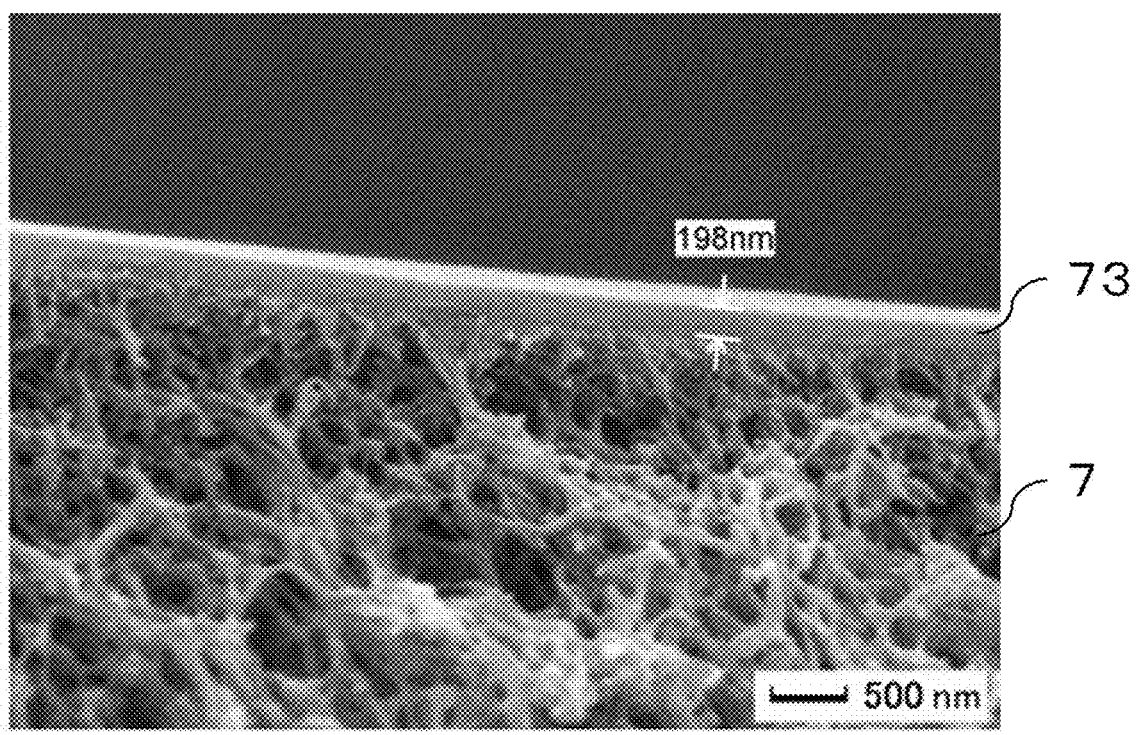
FIG. 7 is a drawing showing SEM images obtained in Examples 2-1, 2-7, 2-9, 2-10, 2-13, 3-1, 3-7, 3-9, 3-10, and 3-13.
Figure 8:
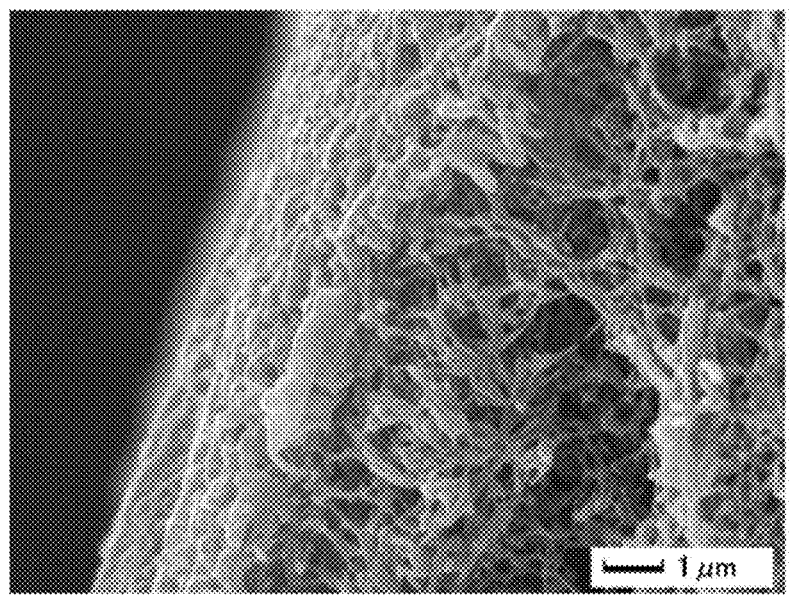
FIG. 8 is a drawing showing SEM images obtained in Examples 2-1, 2-7, 2-9, 2-10, 2-13, 3-1, 3-7, 3-9, 3-10, and 3-13.
Figure 9:
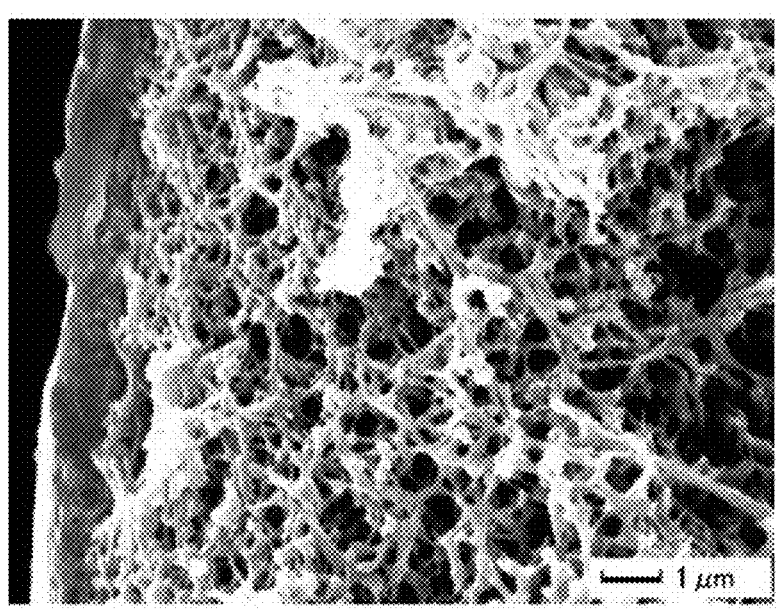
FIG. 9 is a drawing showing SEM images obtained in Examples 2-2 and 3-2.
Figure 10:
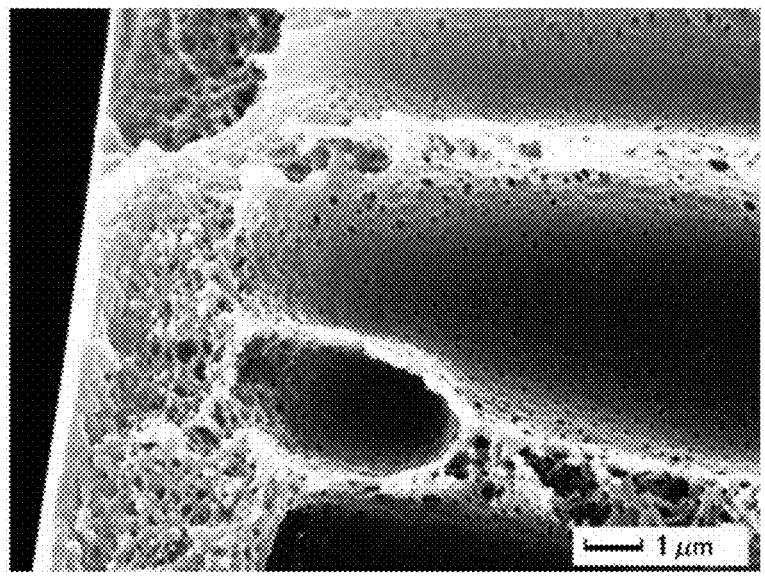
FIG. 10 is a drawing showing SEM images obtained in Examples 2-3, 2-4, 2-5, 3-3, 3-4, and 3-5.
Figure 11:
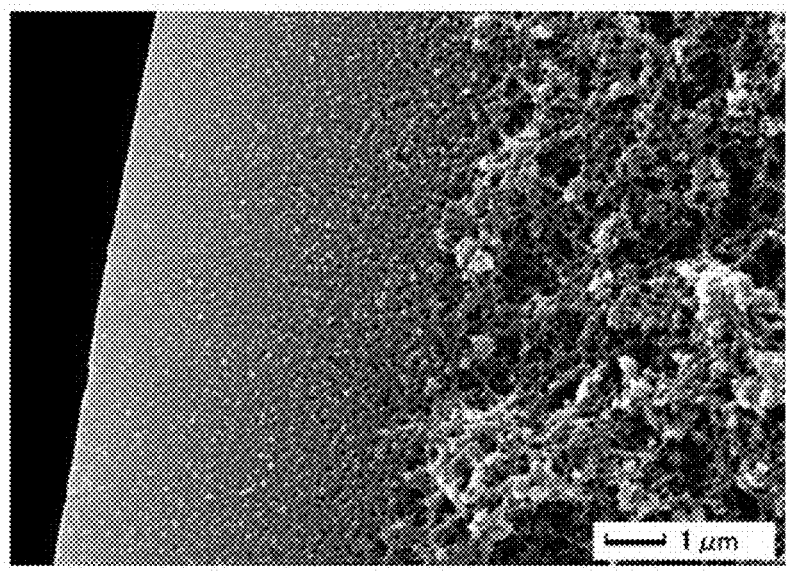
FIG. 11 is a drawing showing SEM images obtained in Examples 2-8, 2-11, 3-8, and 3-11.

A cross sectional SEM image of the gas separation membrane produced in Examples 2-1 is shown in FIG. 7. The results are shown in Table 10.

The coating solutions shown in Table 6 were used and Examples 2-2 to 2-13 were analyzed under the conditions shown in Table 9 in the same manner as Examples 2-1. The SEM images and the results are shown in FIGS. 7 to 11 and Table 10.

TABLE 9

| | Base membrane | | | | | | | Active separation layer | | |
|---|---|---|---|---|---|---|---|---|---|---|
| | material | Dense layer thickness (μm) | av. pore diam. A (μm) | av. pore diam. B (μm) | A/B | shape | Outer diam./inner diam. (μm) | coating solution | material | thickness (μm) |
| Example 2-1 | PVDF | none | 0.32 | 0.8 | 0.38 | hollow fiber | 1160/640 | a | chitosan | 0.2 |
| Example 2-2 | PVDF | 0.5 | 0.1 | 0.8 | 0.13 | hollow fiber | 1230/700 | b | chitosan | 0.2 |
| Example 2-3 | PSU | 0.2 | 0.18 | 0.3 | 0.67 | hollow fiber | 1190/715 | b | chitosan | 0.2 |
| Example 2-4 | PSU | 0.2 | 0.18 | 0.3 | 0.67 | hollow fiber | 1190/715 | c | Nafion | 0.5 |
| Example 2-5 | PSU | 0.2 | 0.18 | 0.3 | 0.67 | hollow fiber | 1190/715 | b | chitosan | 0.2 |
| Example 2-6 | PVDF | none | 0.1 | 0.12 | 0.83 | flat sheet membrane | — | d | chitosan | 5 |
| Example 2-7 | PVDF | none | 0.32 | 0.8 | 0.38 | hollow fiber | 1160/640 | a | chitosan | 0.2 |
| Example 2-8 | PES | 2.3 | 0.01 | 0.5 | 0.5 | hollow fiber | 460/280 | none | none | none |
| Example 2-9 | PVDF | none | 0.32 | 0.8 | 0.38 | hollow fiber | 1160/640 | a | chitosan | 0.2 |
| Example 2-10 | PVDF | none | 0.32 | 0.8 | 0.38 | hollow fiber | 1160/640 | a | chitosan | 0.2 |
| Example 2-11 | PES | 2.3 | 0.01 | 0.5 | 0.5 | hollow fiber | 460/280 | b | chitosan | 0.1 |
| Example 2-12 | PVDF | 2 | 0.01 | 0.1 | 0.1 | hollow fiber | 1130/700 | none | none | none |
| Example 2-13 | PVDF | none | 0.32 | 0.8 | 0.38 | hollow fiber | 1160/640 | a | chitosan | 0.2 |
| Comp. Ex. 2-1 | — | — | — | — | — | — | — | — | — | — |

| | | Pulse NMR analysis value | | Elemental analysis value | | | Hardness analysis | | |
|---|---|---|---|---|---|---|---|---|---|
| | material | adhesive | low-mobility component composition ratio V (%) | signal intensity attenuation rate W (%) | N content $C_N$ | S content $C_S$ | $C_N/C_S$ ratio | value hardness K | humidifying mechanism | Dehydration mechanism |
| Example 2-1 | PVDF | A | 96 | 98 | <0.30 | 0.0050 | <60.0 | 87 | bubble type | alumina |
| Example 2-2 | PVDF | A | 96 | 98 | <0.30 | 0.0050 | <60.0 | 87 | bubble type | alumina |
| Example 2-3 | PSU | D | 79 | 67 | <0.30 | 0.0070 | <42.9 | 47 | bubble type | alumina |
| Example 2-4 | PSU | A | 96 | 98 | <0.30 | 0.0050 | <60.0 | 87 | bubble type | alumina |
| Example 2-5 | PSU | F | 28 | 27 | <0.30 | 0.0050 | <60.0 | 20 | bubble type | alumina |
| Example 2-6 | PVDF | E | 54 | 34 | <0.30 | 0.0070 | <42.9 | 31 | bubble type | alumina |
| Example 2-7 | PVDF | A | 96 | 98 | <0.30 | 0.0050 | <60.0 | 87 | liquid filling | alumina |
| Example 2-8 | PES | A | 96 | 98 | <0.30 | 0.0050 | <60.0 | 87 | bubble type | alumina |
| Example 2-9 | PVDF | J | 93 | 94 | 3.9 | 0.0060 | 650 | 89 | liquid filling | alumina |
| Example 2-10 | PVDF | K | 92 | 83 | 3.8 | 0.0050 | 760 | 74 | bubble type | alumina |
| Example 2-11 | PES | F | 28 | 27 | <0.30 | 0.0050 | <60.0 | 20 | bubble type | alumina |
| Example 2-12 | PVDF | F | 28 | 27 | <0.30 | 0.0050 | <60.0 | 20 | liquid filling | alumina |
| Example 2-13 | PVDF | F | 28 | 27 | <0.30 | 0.0050 | <60.0 | 20 | none | none |
| Comp. Ex. 2-1 | — | — | — | — | — | — | — | — | — | — |

TABLE 10

| | Day 1 | | | | Day 7 | | | | Immediately after gas cylinder exchange | | | |
|---|---|---|---|---|---|---|---|---|---|---|---|---|
| | propylene purity (%) | amount of water (ppm) | paraffin (%) | inorganic impurities (ppm) | propylene purity (%) | amount of water (ppm) | paraffin (%) | inorganic impurities (ppm) | propylene purity (%) | amount of water (ppm) | paraffin (%) | inorganic impurities (ppm) |
| Example 2-1 | 99.999 | 3 | 0.0005 | 2 | 99.999 | 3 | 0.0005 | 2 | — | — | — | — |
| Example 2-2 | 99.993 | 4 | 0.006 | 4 | 99.992 | 4 | 0.007 | 4 | — | — | — | — |
| Example 2-3 | 99.994 | 5 | 0.005 | 4 | 99.99 | 5 | 0.009 | 4 | — | — | — | — |
| Example 2-4 | 99.991 | 5 | 0.008 | 4 | 99.986 | 5 | 0.013 | 3 | — | — | — | — |
| Example 2-5 | 99.982 | 5 | 0.017 | 5 | 99.924 | 5 | 0.075 | 5 | — | — | — | — |
| Example 2-6 | 99.997 | 6 | 0.002 | 5 | 99.997 | 5 | 0.002 | 5 | — | — | — | — |
| Example 2-7 | 99.998 | 5 | 0.001 | 6 | 99.998 | 5 | 0.001 | 6 | — | — | — | — |
| Example 2-8 | 99.922 | 6 | 0.077 | 5 | 99.913 | 5 | 0.086 | 5 | — | — | — | — |
| Example 2-9 | 99.972 | 2 | 0.027 | 8 | 99.999 | 4 | 0.0005 | 1 | — | — | — | — |
| Example 2-10 | 99.997 | 3 | 0.002 | 8 | 99.997 | 3 | 0.002 | 7 | — | — | — | — |
| Example 2-11 | 99.991 | 4 | 0.008 | 6 | 99.744 | 4 | 0.255 | 6 | — | — | — | — |
| Example 2-12 | 99.851 | 4 | 0.148 | 5 | 99.761 | 4 | 0.238 | 5 | — | — | — | — |
| Example 2-13 | 99.808 | 10 | 0.188 | 30 | 99.811 | 10 | 0.185 | 32 | — | — | — | — |
| Comp. Ex. 2-1 | 99.995 | 10 | 10 | 30 | 99.995 | 10 | 10 | 30 | 68.384 | 588 | 0.193 | 30.927 |

"FC-4430" in the table is a fluorine-based surfactant having a perfluoroalkyl group manufactured by 3M, product name "Novec FC-4430", and "Nafion" is a registered trademark (the same applies below).

Comparative Example 2-1

Measurement was carried out using a commercially available high purity propylene gas cylinder without using a gas purification system.

The results on day 1 were calculated from the composition 3 hours after the start of supply of a high purity propylene gas. The results on day 7 were obtained 7 days after the start of the supply. Further, results were obtained from the composition immediately after changing the gas cylinder. The separation gas was analyzed by gas chromatography (GC).

The analysis results are shown in Table 4.

The purity of the purified gas immediately after changing the gas cylinder was significantly decreased. It took about 15 h to purify the gas again to 99.99% by mass or more.

<Performance Test of an On-Site High Purity Gas Supply System>

A gas separation membrane was immersed in 0.8 M sodium hydroxide solution (solvent=ethanol:water (80:20 by volume)) for 1 day, and was thereafter washed 5 times with distilled water. This gas separation membrane was cut to 15 cm. 10 pieces were formed into one bundle to form a gas separation membrane module using the adhesive shown in Table 3. Thereafter, this gas separation membrane module was immersed in 7 M aqueous silver nitrate solution for 24 h to obtain a gas separation membrane containing a silver salt. This gas separation membrane containing a silver salt was used to measure the permeation rates of propane and propylene.

Examples 3-1 to 3-6, 3-8, and 3-11 were measured using a gas purification system in which 99.5% by mass of propylene (containing propane, carbon monoxide, carbon dioxide, ammonia, oxygen, nitrogen, NOx, etc., as impurities) containing water vapor added in a bubble type manner at 28.5° C. was supplied at 190 cc/min and 30° C. to a membrane module for gas separation, and was dehydrated by an alumina adsorbent.

Examples 3-7 and 3-12 were measured using a gas purification system in which 99.5% by mass of propylene (containing propane, carbon monoxide, carbon dioxide, ammonia, oxygen, nitrogen, NOx, etc., as impurities) was supplied at 190 cc/min and 30° C. to a membrane module for gas separation loaded with 7 M aqueous silver nitrate solution, and was dehydrated by an alumina adsorbent. Examples 3-13 was measured using a gas purification system in which 99.5% by mass of propylene (containing propane, carbon monoxide, carbon dioxide, ammonia, oxygen, nitrogen, NOx, etc., as impurities) was directly supplied at 190 cc/min and 30° C. to a membrane module for gas separation.

The results on day 1 were calculated from the composition of a gas which were discharged from a gas purification system, 3 hours after the start of supply of the raw material gas. The results on day 7 were obtained 7 days after the start of the supply.

Example 3-1

A hollow fiber made of polyvinylidene fluoride was used as a porous membrane. The outer diameter, the inner diameter, and the average pore diameters A and B thereof are shown in Table 11.

The length of the hollow fiber support was 25 cm. Both ends were heat sealed. The hollow fiber support was immersed into a coating solution A (liquid temperature 25° C.) having the following composition at a rate of 1 cm/sec. The whole of the support was submerged in the above aqueous solution and was left standing for 5 sec. Thereafter, the support was pulled out at a rate of 1 cm/sec, and was heated at 120° C. for 10 min to form a gas separation active layer on an outer surface of the hollow fiber support, whereby a hollow fiber gas separation membrane was produced.

A cross-sectional SEM image of the gas separation membrane produced in Example 3-1 is shown in FIG. 7. The results are shown in Table 12.

The coating solutions shown in Table 6 were used and Examples 3-2 to 3-13 were analyzed under the conditions shown in Table 11 in the same manner as Examples 3-1. The results are shown in Table 12.

TABLE 11

| | Base membrane | | | | | | | Active separation layer | | |
|---|---|---|---|---|---|---|---|---|---|---|
| | material | Dense layer thickness (μm) | av. pore diam. A (μm) | av. pore diam. B (μm) | A/B | shape | Outer diam./ inner diam. (μm) | coating solution | material | thickness (μm) |
| Example 3-1 | PVDF | none | 0.32 | 0.8 | 0.38 | hollow fiber | 1160/640 | a | chitosan | 0.2 |
| Example 3-2 | PVDF | 0.5 | 0.1 | 0.8 | 0.13 | hollow fiber | 1230/700 | b | chitosan | 0.2 |
| Example 3-3 | PSU | 0.2 | 0.18 | 0.3 | 0.67 | hollow fiber | 1190/715 | b | chitosan | 0.2 |
| Example 3-4 | PSU | 0.2 | 0.18 | 0.3 | 0.67 | hollow fiber | 1190/715 | c | Nafion | 0.5 |
| Example 3-5 | PSU | 0.2 | 0.18 | 0.3 | 0.67 | hollow fiber | 1190/715 | b | chitosan | 0.2 |
| Example 3-6 | PVDF | none | 0.1 | 0.12 | 0.83 | flat sheet membrane | — | d | chitosan | 5 |
| Example 3-7 | PVDF | none | 0.32 | 0.8 | 0.38 | hollow fiber | 1160/640 | a | chitosan | 0.2 |
| Example 3-8 | PES | 2.3 | 0.01 | 0.5 | 0.5 | hollow fiber | 460/280 | none | none | none |
| Example 3-9 | PVDF | none | 0.32 | 0.8 | 0.38 | hollow fiber | 1160/640 | a | chitosan | 0.2 |
| Example 3-10 | PVDF | none | 0.32 | 0.8 | 0.38 | hollow fiber | 1160/640 | a | chitosan | 0.2 |
| Example 3-11 | PES | 2.3 | 0.01 | 0.5 | 0.5 | hollow fiber | 460/280 | b | chitosan | 0.1 |
| Example 3-12 | PVDF | 2 | 0.01 | 0.1 | 0.1 | hollow fiber | 1130/700 | none | none | none |
| Example 3-13 | PVDF | none | 0.32 | 0.8 | 0.38 | hollow fiber | 1160/640 | a | chitosan | 0.2 |
| Comp. Ex. 3-1 | — | — | — | — | — | — | — | — | — | — |

| | | Pulse NMR analysis value | | Elemental analysis value | | | Hardness analysis | | |
|---|---|---|---|---|---|---|---|---|---|
| | adhesive | low-mobility component composition ratio V (%) | signal intensity attenuation rate W (%) | N content $C_N$ | S content $C_S$ | $C_N/C_S$ ratio | value hardness K | Humidifying mechanism | Dehydration mechanism |
| Example 3-1 | A | 96 | 98 | <0.30 | 0.0050 | <60.0 | 87 | bubble type | alumina |
| Example 3-2 | A | 96 | 98 | <0.30 | 0.0050 | <60.0 | 87 | bubble type | alumina |
| Example 3-3 | D | 79 | 67 | <0.30 | 0.0070 | <42.9 | 47 | bubble type | alumina |
| Example 3-4 | A | 96 | 98 | <0.30 | 0.0050 | <60.0 | 87 | bubble type | alumina |
| Example 3-5 | F | 28 | 27 | <0.30 | 0.0050 | <60.0 | 20 | bubble type | alumina |
| Example 3-6 | E | 54 | 34 | <0.30 | 0.0070 | <42.9 | 31 | bubble type | alumina |
| Example 3-7 | A | 96 | 98 | <0.30 | 0.0050 | <60.0 | 87 | liquid filling | alumina |
| Example 3-8 | A | 96 | 98 | <0.30 | 0.0050 | <60.0 | 87 | bubble type | alumina |
| Example 3-9 | J | 93 | 94 | 3.9 | 0.0060 | 650 | 89 | liquid filling | alumina |
| Example 3-10 | K | 92 | 83 | 3.8 | 0.0050 | 760 | 74 | bubble type | alumina |
| Example 3-11 | F | 28 | 27 | <0.30 | 0.0050 | <60.0 | 20 | bubble type | alumina |
| Example 3-12 | F | 28 | 27 | <0.30 | 0.0050 | <60.0 | 20 | liquid filling | alumina |
| Example 3-13 | F | 28 | 27 | <0.30 | 0.0050 | <60.0 | 20 | none | none |
| Comp. Ex. 3-1 | — | — | — | — | — | — | — | — | — |

TABLE 12

| | Day 1 | | | | Day 7 | | | | Immediately after gas cylinder exchange | | | |
|---|---|---|---|---|---|---|---|---|---|---|---|---|
| | propylene purity (%) | amount of water (ppm) | paraffin (%) | inorganic impurities (ppm) | propylene purity (%) | amount of water (ppm) | paraffin (%) | inorganic impurities (ppm) | propylene purity (%) | amount of water (ppm) | paraffin (%) | inorganic impurities (ppm) |
| Example 3-1 | 99.999 | 3 | 0.0005 | 2 | 99.999 | 3 | 0.0005 | 2 | — | — | — | — |
| Example 3-2 | 99.993 | 4 | 0.006 | 4 | 99.992 | 4 | 0.007 | 4 | — | — | — | — |
| Example 3-3 | 99.994 | 5 | 0.005 | 4 | 99.99 | 5 | 0.009 | 4 | — | — | — | — |

TABLE 12-continued

|  | Day 1 | | | | Day 7 | | | | Immediately after gas cylinder exchange | | | |
| --- | --- | --- | --- | --- | --- | --- | --- | --- | --- | --- | --- | --- |
|  | propylene purity (%) | amount of water (ppm) | paraffin (%) | inorganic impurities (ppm) | propylene purity (%) | amount of water (ppm) | paraffin (%) | inorganic impurities (ppm) | propylene purity (%) | amount of water (ppm) | paraffin (%) | inorganic impurities (ppm) |
| Example 3-4 | 99.991 | 5 | 0.008 | 4 | 99.986 | 5 | 0.013 | 3 | — | — | — | — |
| Example 3-5 | 99.982 | 5 | 0.017 | 5 | 99.924 | 5 | 0.075 | 5 | — | — | — | — |
| Example 3-6 | 99.997 | 6 | 0.002 | 5 | 99.997 | 5 | 0.002 | 5 | — | — | — | — |
| Example 3-7 | 99.998 | 5 | 0.001 | 6 | 99.998 | 5 | 0.001 | 6 | — | — | — | — |
| Example 3-8 | 99.922 | 6 | 0.077 | 5 | 99.913 | 5 | 0.086 | 5 | — | — | — | — |
| Example 3-9 | 99.972 | 2 | 0.027 | 8 | 99.999 | 4 | 0.0005 | 1 | — | — | — | — |
| Example 3-10 | 99.997 | 3 | 0.002 | 8 | 99.997 | 3 | 0.002 | 7 | — | — | — | — |
| Example 3-11 | 99.991 | 4 | 0.008 | 6 | 99.744 | 4 | 0.255 | 6 | — | — | — | — |
| Example 3-12 | 99.851 | 4 | 0.148 | 5 | 99.761 | 4 | 0.238 | 5 | — | — | — | — |
| Example 3-13 | 99.808 | 10 | 0.188 | 30 | 99.811 | 10 | 0.185 | 32 | — | — | — | — |
| Comp. Ex. 3-1 | 99.995 | 10 | 10 | 30 | 99.995 | 10 | 10 | 30 | 68.384 | 588 | 0.193 | 30.927 |

Comparative Example 3-1

Measurement was carried out using a commercially available high purity propylene gas cylinder without using a gas purification system.

The results on day 1 were calculated from the composition 3 hours after the start of supply of a high purity propylene gas. The results on day 7 were obtained 7 days after the start of the supply. Further, results were obtained from the composition immediately after changing the gas cylinder. The separation gas was analyzed by gas chromatography (GC).

The analysis results are shown in Table 12.

The purity of the purified gas immediately after changing the gas cylinder was significantly decreased. It took about 15 h to purify the gas again to 99.99% by mass or more.

<Infrared Spectroscopic Analysis of an Adhesive Cured Product>

Analysis Examples 4-1 to 4-3

Figure 6:
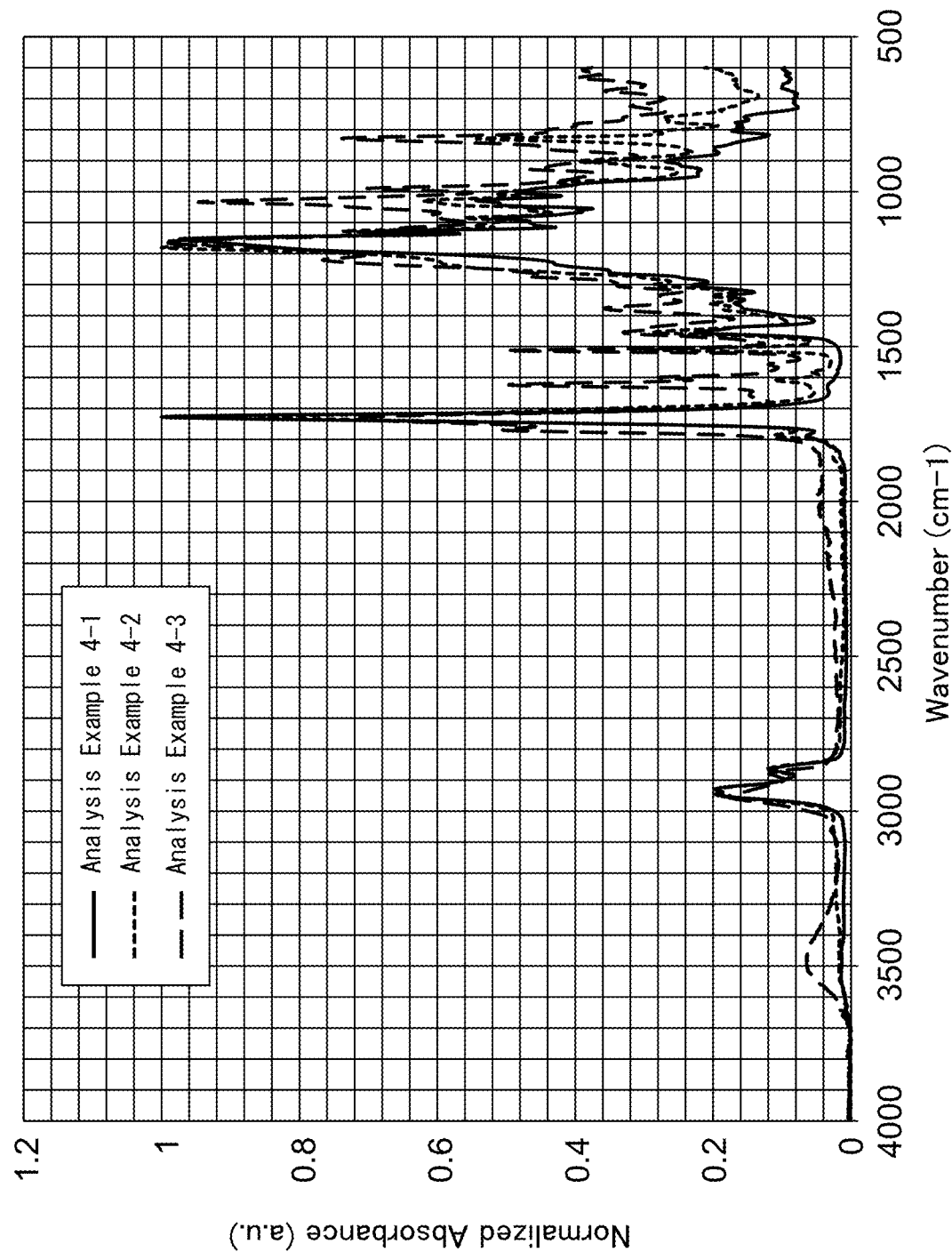
FIG. 6 is a drawing showing infrared ATR charts measured in Analysis Examples 4-1 to 4-3.

A plate-like body (70 mm×5 mm×1 mm) was formed from a cured product of an adhesive using each of adhesive A (Analysis Example 4-1), adhesive D (Analysis Example 4-2), and adhesive E (Analysis Example 4-3) at the mixing ratio of a base resin and a curing agent under the curing conditions shown in Table 1. The obtained plate-like body was dried at 50° C. under reduced pressure for 24 h. Thereafter, infrared spectroscopic analysis was carried out under the following conditions.
IR device: Type "LUMOS" available from Bruker
  Measurement method: ATR method (Ge crystal)
  Wavenumber Resolution: 4 cm$^{-1}$
  Number of integrations: 64 times
  Measurement area: 50 μm×50 μm
  Analysis depth: less than 1 μm
The obtained infrared ATR chart is shown in FIG. 6.

From the above Examples, it was verified that a membrane module for gas separation has long-term highly practical permeation performance and separation performance, wherein an adhesive part of the membrane module for gas separation satisfies at least one of the following (1) to (6):
1) the adhesive part has a low-mobility component having a composition ratio V (%), as measured by pulse NMR, wherein 30≤V≤100;
2) the adhesive part has an attenuation rate W (%) represented by the following formula:

$$W=[(I1-I2)/I1]\times 100$$

wherein I1 is a signal intensity at the start of measurement in the pulse NMR of the adhesive part, I2 is a signal intensity 0.05 msec after the measurement starts, and
wherein 30≤W≤100;
3) the adhesive part has a change ratio X (%) represented by the following formula:

$$X=[(V2-V1)/V1]\times 100$$

wherein V1 and V2 respectively represent the composition rates V(V1(%)) and V(V2(%)) before and after immersion of the adhesive part in a 7 mol/L aqueous silver nitrate solution or heptane for 1 month at 25° C., and
wherein −50≤X≤50;
4) the adhesive part has a change ratio Y (%) represented by the following formula:

$$Y=[(W2-W1)/W1]\times 100$$

wherein W1 and W2 respectively represent the attenuation rates W(W1(%)) and W(W2(%)) before and after immersion of the adhesive part in a 7 mol/L aqueous silver nitrate solution or heptane for 1 month at 25° C., respectively, and
wherein −120≤Y≤120;
5) the adhesive part has a nitrogen atom content ($C_N$, % by mass), wherein 0.0010≤$C_N$≤10, and a sulfur atom content ($C_S$, % by mass), wherein 0.0010≤$C_S$≤0.01; and
6) the adhesive part has a hardness K, wherein 10D≤K≤90D.

This is probably because swelling and degradation due to a gas to be separated, a metal salt, etc., is suppressed, whereby collapse of the adhesive, leakage of a gas used, mixing of a raw material gas with a purified gas, damage of a housing part, peeling of an adhesive part from a porous membrane or a gas separation active layer, etc., do not occur.

INDUSTRIAL APPLICABILITY

When the membrane module for gas separation of the present embodiment is used, an energy saving and highly safe gas separation method (a method of separation of, in particular, an olefin gas, etc.) is provided.

REFERENCE SIGNS LIST 1 porous membrane
2 housing
3 footer part
4 header part
5 gas separation active layer
6 gas separation membrane
10 adhesive part
11 plate-like member
21 gas supply port
22 process gas outlet
31 permeable gas inlet
41 separation gas outlet
7 porous membrane
71 depth range for determining an average pore diameter A
72 depth range for determining an average pore diameter B
73 gas separation active layer
74 pore
8 raw-gas purification part
81 raw material gas inlet
82 purified gas outlet
9 membrane module for gas separation
91 humidifying mechanism
92 dehydration mechanism
100 and 200 membrane module for gas separation
700 gas separation membrane
800 continuous gas supply system
900 membrane module unit

The invention claimed is:

1. A membrane module for gas separation, comprising:
a housing;
a gas separation membrane disposed in the housing; and
an adhesive part for affixing the gas separation membrane to the housing, wherein
the gas separation membrane is composed of a porous membrane,
the adhesive part satisfies at least one of the following (1) to (6):
1) the adhesive part has a low-mobility component having a composition ratio V (%), as measured by pulse NMR, wherein $30 \leq V \leq 100$;
2) the adhesive part has an attenuation rate W (%) represented by the following formula:

$$W=[(I1-I2)/I1] \times 100$$

wherein I1 is a signal intensity at start of measurement in the pulse NMR of the adhesive part, I2 is a signal intensity 0.05 msec after the measurement starts, and
wherein $30 \leq W \leq 100$;
3) the adhesive part has a change ratio X (%) represented by the following formula:

$$X=[(V2-V1)/V1] \times 100$$

wherein V1 and V2 respectively represent the composition rates V(V1(%)) and V(V2(%)) before and after immersion of the adhesive part in a 7 mol/L aqueous silver nitrate solution or heptane for 1 month at 25° C., and
wherein $-50 \leq X \leq 50$;
4) the adhesive part has a change ratio Y (%) represented by the following formula:

$$Y=[(W2-W1)/W1] \times 100$$

wherein W1 and W2 respectively represent the attenuation rates W(W1(%)) and W(W2(%)) before and after immersion of the adhesive part in a 7 mol/L aqueous silver nitrate solution or heptane for 1 month at 25° C., respectively, and
wherein $-120 \leq Y \leq 120$;
5) the adhesive part has a nitrogen atom content ($C_N$, % by mass), wherein $0.0010 \leq C_N \leq 10$, and a sulfur atom content ($C_S$, % by mass), wherein $0.0010 \leq C_S \leq 0.01$; and
6) the adhesive part has a hardness K, wherein $10D \leq K \leq 90D$.

2. The membrane module for gas separation according to claim 1, wherein the composition ratio V of the adhesive part is $50 \leq V \leq 100$.

3. The membrane module for gas separation according to claim 2, wherein the composition ratio V of the adhesive part is $70 \leq V \leq 100$.

4. The membrane module for gas separation according to claim 3, wherein the composition ratio V of the adhesive part is $90 \leq V \leq 100$.

5. The membrane module for gas separation according to claim 1, wherein the attenuation rate W of the adhesive part is $60 \leq W \leq 100$.

6. The membrane module for gas separation according to claim 5, wherein the attenuation rate W of the adhesive part is $90 \leq W \leq 100$.

7. The membrane module for gas separation according to claim 6, wherein the change ratio X of the adhesive part is $-25 \leq X \leq 25$.

8. The membrane module for gas separation according to claim 7, wherein the change ratio Y of the adhesive part is $-60 \leq Y \leq 60$.

9. The membrane module for gas separation according to claim 1, wherein the nitrogen atom content $C_N$ of the adhesive part is $0.0010 \leq C_N \leq 4.0$.

10. The membrane module for gas separation according to claim 9, wherein the nitrogen atom content $C_N$ of the adhesive part is $0.0010 \leq C_N \leq 0.30$.

11. The membrane module for gas separation according to claim 1, wherein the sulfur atom content $C_S$ of the adhesive part is $0.0010 \leq C_S \leq 0.0070$.

12. The membrane module for gas separation according to claim 1, wherein the hardness K of the adhesive part is $30D \leq K \leq 90D$.

13. The membrane module for gas separation according to claim 12, wherein the hardness K of the adhesive part is $50D \leq K \leq 90D$.

14. The membrane module for gas separation according to claim 1, wherein a change ratio of a bending Young's modulus and a change ratio of a bending strength after and before immersion of the adhesive part in a 7 mol/L aqueous silver nitrate solution or heptane for 1 month at 25° C. are each within a range of −30% to +30%.

15. The membrane module for gas separation according to claim 1, wherein a change in mass per surface area of the test piece after and before immersion of the adhesive part in a 7 mol/L aqueous silver nitrate solution or heptane for 1 month at 25° C. is within a range of −30 mg/cm$^2$ to +30 mg/cm$^2$.

16. The membrane module for gas separation according to claim 15, wherein a change ratio of the thickness of the test piece after and before immersion of the adhesive part in a 7 mol/L aqueous silver nitrate solution or heptane for 1 month at 25° C. is within a range of −5% to +5%.

17. The membrane module for gas separation according to claim 1, wherein the adhesive part does not substantially contain a cured product of a fluorine thermoplastic resin.

18. The membrane module for gas separation according to claim 1, wherein the gas separation membrane comprises a metal salt containing monovalent Ag and/or monovalent Cu.

19. The membrane module for gas separation according to claim 1, wherein a permeation rate of propylene gas is 10 GPU to 3,000 GPU and a separation factor of propylene/ propane is 50 to 1,000, as measured using a mixed gas composed of 40% by mass of propane and 60% by mass of propylene with respect to the membrane module for gas separation at a supply side gas flow rate of 190 cc/min per 2 cm$^2$ membrane area and a permeation side gas flow rate of 50 cc/min per 2 cm$^2$ membrane area in a humidified atmosphere under isobaric conditions at 30° C.

20. A continuous gas supply system, wherein the continuous gas supply system is of a gas flow type and comprises a raw material gas inlet, a raw-gas purification part for purifying a raw material gas to generate a purified gas, and a purified gas outlet, and the raw-gas purification part is composed of the membrane module for gas separation according to claim 1.

21. The continuous gas supply system according to claim 20, wherein the purified gas has a purity of 99.5% by mass or higher.

* * * * *